(12) United States Patent
DeWildt

(10) Patent No.: US 7,846,721 B2
(45) Date of Patent: Dec. 7, 2010

(54) GAS1 UNIVERSAL LEADER

(75) Inventor: Rudolph M. T. DeWildt, Cambridge (GB)

(73) Assignee: Domantis Limited, Cambridge (GB)

( * ) Notice: Subject to any disclaimer, the term of this patent is extended or adjusted under 35 U.S.C. 154(b) by 0 days.

(21) Appl. No.: 11/494,965

(22) Filed: Jul. 27, 2006

(65) Prior Publication Data

US 2007/0026462 A1    Feb. 1, 2007

Related U.S. Application Data

(63) Continuation of application No. PCT/GB2005/001180, filed on Mar. 24, 2005.

(60) Provisional application No. 60/555,764, filed on Mar. 24, 2004.

(51) Int. Cl.
*C12N 5/00*    (2006.01)
*C12Q 1/68*    (2006.01)
*C07H 21/02*    (2006.01)

(52) U.S. Cl. .................. 435/320.1; 435/6; 536/23.1
(58) Field of Classification Search .............. 435/320.1, 435/6; 536/23.1
See application file for complete search history.

(56) References Cited

U.S. PATENT DOCUMENTS 6,555,310 B1    4/2003   Gray et al. .................. 435/5

FOREIGN PATENT DOCUMENTS

| WO | WO 95/22614 | | 8/1995 |
|---|---|---|---|
| WO | WO 03/068956 | * | 8/2003 |
| WO | WO03/068956 A1 | | 8/2003 |

OTHER PUBLICATIONS

Humphreys et al., 2000, High-Level Periplasmic Expression in *Escherichia coli* Using a Eukaryotic Signal Peptide: Importance of Codon Usage a the 5' End of the Coding Sequence, Protein Expression and Purification, 20: 252-264.*

Wada et al., 1991, Codon usage tabulated from the GenBank genetic sequence data, Nucleic Acids Research, 19: 1981-1986.*

Wada et al., 1992, Codon usage tabulated from the GenBank genetic sequence data, Nucleic Acids Research, 20: 2111-2118.*

Nuoffer, et al., "Determinants for Glycophospholipid Anchoring of the *Saccharomyces cerevisae* GAS1 Protein to the Plasma Membrane," Molecular and Cellular Biology (Jan. 1991), p. 27-37.

Pignatelli, et al., "Expression and secretion of β-galactosidase in *Saccharomyces cerevisiae* using the signal sequences of GgpI, the major yeast glycosylphosphatidylinositol-containing protein," Biotechnol. Appl. Biochem., vol. 27 (1998), p. 81-88.

Vai, et al., "Isolation and Deduced Amino Acid Sequence of the Gene Encoding gp115, a Yeast Glycophospholipid-anchored Protein Containing a Serine-rich Region," Journal of Biological Chemistry, vol. 266, No. 19 (Jul. 5, 1991), p. 12242-12248.

Watson, Marion E.E., "Compilation of published signal sequences," Nucl. Acids Res., vol. 12, No. 13 (1984), p. 5154-5164.

* cited by examiner

*Primary Examiner*—Amber D. Steele
(74) *Attorney, Agent, or Firm*—William Peter Long; William T. Han

(57) ABSTRACT

Disclosed is a polynucleotide molecule comprising a promoter operably linked to a nucleic acid sequence encoding a GAS1 secretion signal peptide, wherein said promoter is not a rhamnose promoter.

10 Claims, 8 Drawing Sheets

```
                    (1) 1         10        20        30        40        50        66
         GAS wt     (1) ATGTTGTTTAAATCCCTTTCAAAGTTAGCAACCGCTGCTGCTTTTTTTGCTGGCGTCGCAACTGCG
    GAS leader e.coli (1) ATGCTGTTTAAAAGCCTGAGCAAACTGGCGACCGCGCCGCCGTTTTTTGCGGGCGTGGCGACCGCG
       GAS leaderAT (1) ATGTTATTTAAATCATTATCAAAATTAGCAACCGCAGCAGCATTTTTTGCAGGCGTGGCAACAGCG
```

Figure 1: Nucleotide sequence comparison of GAS leader variants.

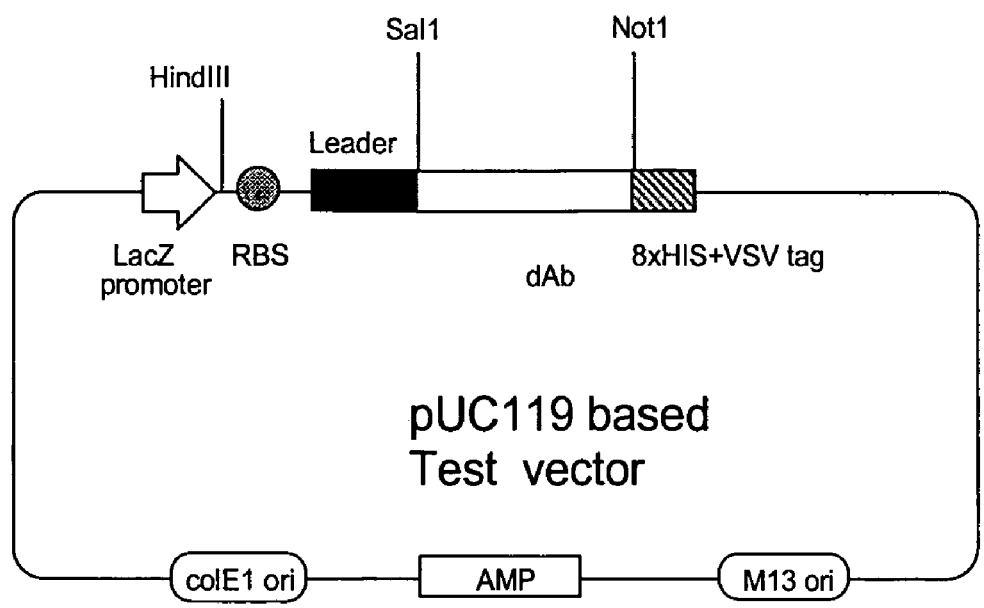
Figure 2: Expression vector map for test of signal peptides

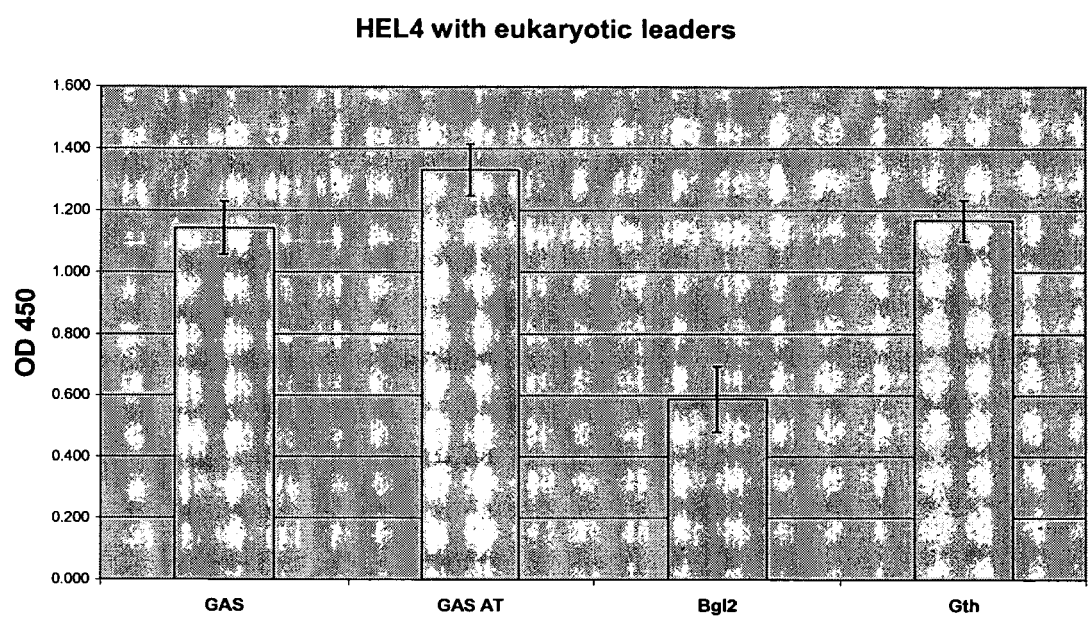
Figure 3: Signal peptides in antigen binding ELISA.
GAS = Yeast GAS1; GAS AT = Yeast GAS1 (AT rich); Bgl2 = Yeast BGL2
Gth = GTH1 ONCKE. Error bars indicate standard deviation of 4 measurements.

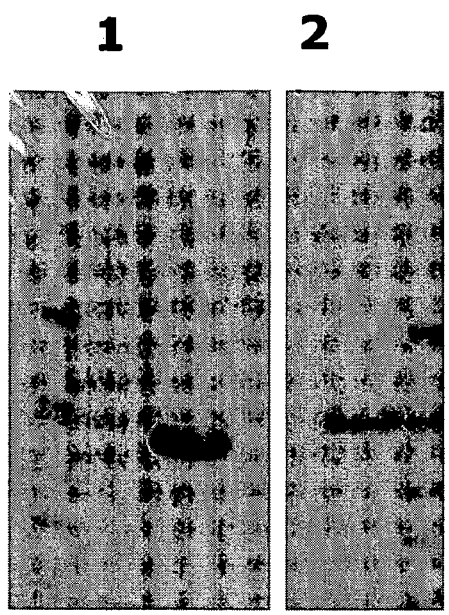

Figure 4: Expression levels of dAb HEL4 with GAS signal peptide.

dAbs were purified from 50 ml culture supernatants using protein A Sepharose in a batch wise manner. Purified dAbs were analyzed on a SDS PAGE. Lane 1: GAS AT rich signal peptide; Lane 2: gene3 signal peptide with N terminal FLAG tag. Expression levels were determined using OD280. Lane 1: GAS 32 mg/l; Lane 2: gene3 with FLAG tag 14.3 mg/l.

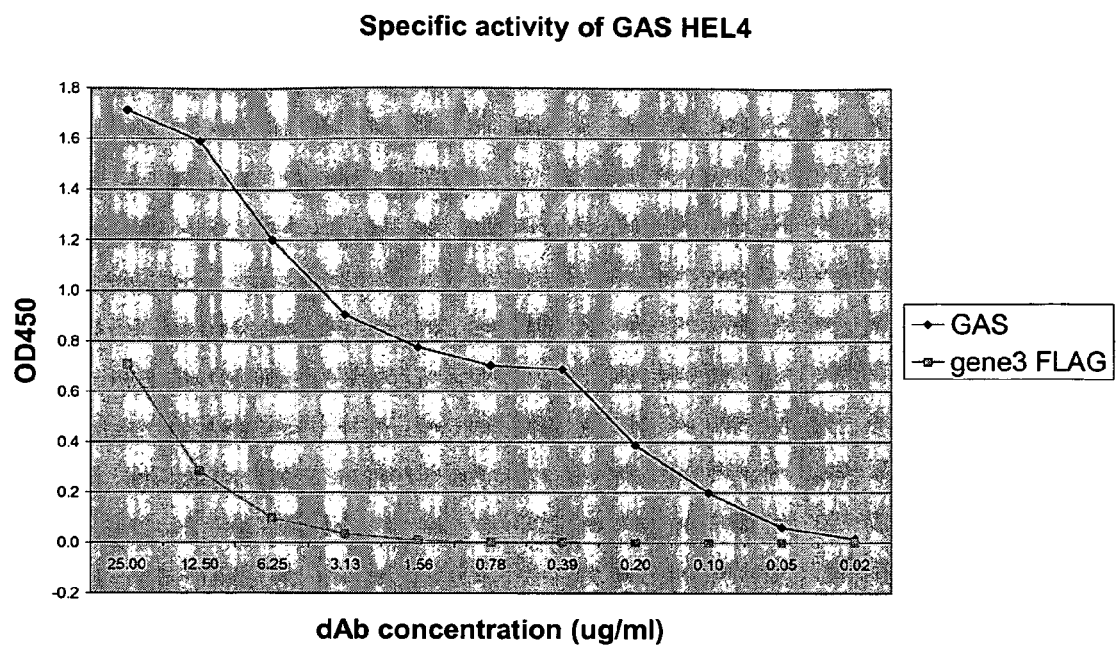
Figure 5: Specific activity of dAb HEL4 with GAS signal peptide.
Comparison of binding of dAb HEL4 produced with GAS AT rich signal peptide and gene3 signal peptide. Lysozyme was coated to an ELISA plate and binding dAbs were detected using the VSV tag. Indicated values are means of two independent measurements.

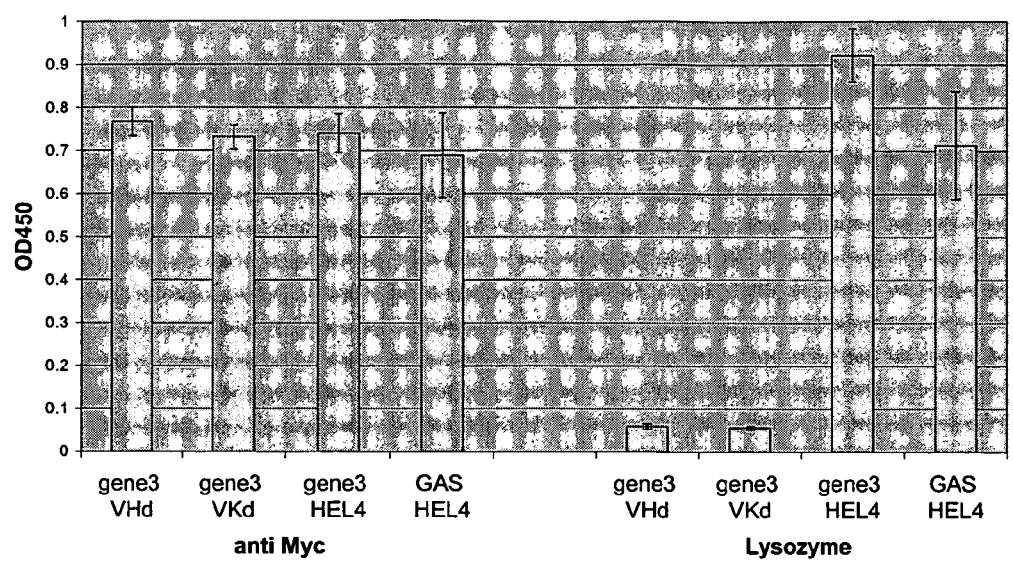
Figure 6: Specific activity of dAb HEL4 with GAS signal peptide.
Comparison of binding of dAb HEL4 produced with GAS AT rich signal peptide and gene3 signal peptide. Lysozyme or anti-myc antibody was coated to an ELISA plate and binding phage was detected using anti-M13 HRP conjugate antibody.

GAS1 UNIVERSAL LEADER

RELATED APPLICATIONS

This application is a Continuation of International Application No. PCT/GB2005/001180, filed Mar. 24, 2005, which designated the United States and published in English on Oct. 6, 2005. This application claims priority under 35 U.S.C. §119(e) to U.S. application Ser. No. 60/555,764, filed Mar. 24, 2004. These priority applications are incorporated herein in their entirety by reference.

BACKGROUND

Secretion signal peptides assist proteins in traversing cell membranes. They are used by both prokaryotes, such as *E. coli*, and eukaryotic cells. The vast majority of secretory proteins do not share a uniform consensus sequence (Watson, Nucl. Acids. Res. 12:5145 (1984)). In fact they are quite divergent. Substitutions between signal sequences of different species is highly unpredictable and usually results in inconsistent secretion between species, e.g., prokaryotes and eukaryotes. Few signal sequences result in efficient secretion in both prokaryotes and eukaryotes.

There is a significant interest in producing recombinant proteins in a secreted form. Secretion allows for easy recovery of the recombinant protein of interest from the medium in which the host cell is grown.

SUMMARY OF THE INVENTION

The invention provides compositions and methods for enhanced polypeptide secretion through use of secretion signal polypeptides. In one embodiment, the compositions and methods are particularly useful for generating an immunoglobulin variable domain polypeptide library and for the generation of single domain antibodies themselves.

The invention further relates to polynucleotide molecules comprising GAS1 secretion signal polypeptides (SEQ ID NO: 2). Particularly GAS1 secretion signal polypeptides which have been optimized for bacterial expression. An optimized nucleic acid sequence encoding a GAS1 secretion signal peptide is preferably the nucleic acid sequence of SEQ ID No: 3 or 4. In a preferred embodiment the polynucleotide molecule comprising the GAS1 secretion signal polypeptide is operably linked to an immunoglobulin variable domain polypeptide.

In a first aspect of the invention, a polynucleotide molecule (including, e.g., an isolated polynucleotide molecule) is disclosed comprising a polynucleotide molecule comprising a promoter operably linked to a nucleic acid sequence encoding a GAS1 secretion signal peptide, wherein the promoter is not a rhamnose promoter.

In one embodiment, the polynucleotide molecule is operably linked to a nucleic acid sequence encoding a heterologous polypeptide.

In another aspect, a polynucleotide molecule is disclosed comprising a nucleic acid sequence encoding a GAS1 secretion signal peptide operably linked to a nucleic acid sequence encoding a heterologous polypeptide, wherein the polynucleotide molecule comprises a restriction endonuclease cleavage site between the sequence encoding the GAS1 secretion signal peptide and the sequence encoding the heterologous polypeptide.

In another aspect, a library of polynucleotide molecules is disclosed, wherein each molecule of said library comprises a promoter operably linked to a sequence encoding a GAS1 secretion signal polypeptide which is in turn linked to a nucleic acid sequence encoding a heterologous polypeptide, wherein said promoter is not a rhamnose promoter.

In another aspect of the invention, a polynucleotide molecule is disclosed comprising a polynucleotide molecule comprising a promoter operably linked to a nucleic acid sequence encoding a GAS1 secretion signal peptide. The polynucleotide encoding a GAS1 secretion signal peptide is in turn operably linked to a nucleic acid sequence encoding an immunoglobulin variable domain polypeptide, wherein the promoter is not a rhamnose promoter.

In one embodiment of the composition, the sequence encoding the GAS1 secretion signal peptide is optimized for expression in a bacteria.

In another embodiment, the sequence encoding the GAS1 secretion signal peptide is the sequence of SEQ ID NO: 3.

In another embodiment, the sequence encoding the GAS1 secretion signal peptide is the sequence of SEQ ID NO: 4.

In another embodiment, the immunoglobulin variable domain polypeptide comprises a light chain variable domain ($V_L$).

In another embodiment, the immunoglobulin variable domain polypeptide comprises a heavy chain variable domain ($V_H$).

In another embodiment, the sequence encoding a GAS1 secretion signal peptide is operably linked at its 3' end to a bacteriophage coat protein.

In another embodiment of the invention, a polynucleotide library is disclosed comprising a plurality of nucleic acid molecules of the invention.

In another embodiment of the invention host cells are transformed with the polynucleotide of the invention.

In another embodiment of the invention, a bacteriophage is disclosed the bacteriophage comprising the polynucleotide of the invention.

In still another embodiment of the invention, the GAS1 secretion signal peptide is a *S. cerevisiae* GAS1 secretion signal peptide.

In another aspect of the invention, a polynucleotide molecule is disclosed comprising a promoter operably linked to a nucleic acid sequence encoding a GAS1 secretion signal peptide, which is in turn operably linked to a nucleic acid sequence encoding a single immunoglobulin variable domain polypeptide.

In a first embodiment of this aspect, the sequence encoding the GAS1 secretion signal peptide is optimized for expression in a bacteria.

In a further embodiment, the sequence encoding a GAS1 secretion signal peptide is the sequence of SEQ ID NO: 3.

In another embodiment, the sequence encoding a GAS1 secretion signal peptide is the sequence of SEQ ID NO: 4.

In another embodiment, the single immunoglobulin variable domain polypeptide comprises a light chain variable domain ($V_L$).

In another embodiment, the single immunoglobulin variable domain polypeptide comprises a heavy chain variable domain ($V_H$).

In another embodiment the sequence encoding the GAS1 secretion signal peptide is operably linked at its 3' end to a bacteriophage coat protein.

In another embodiment of the invention, a polynucleotide library is disclosed comprising a plurality of nucleic acid molecules according to the invention.

In yet another embodiment, a host cell is disclosed, wherein the host cell is transformed with the polynucleotide of the invention.

In yet another embodiment, a bacteriophage is disclosed, wherein the bacteriophage comprises the polynucleotide of the invention.

In another embodiment, the GAS1 secretion signal peptide is a *S. cerevisiae* GAS1 secretion signal peptide.

In another aspect, a polynucleotide molecule encoding a secretable immunoglobulin chain is disclosed, the polynucleotide molecule comprising a nucleic acid encoding a GAS1 secretion signal peptide operably linked to a nucleic acid encoding a polypeptide selected from the group consisting of an immunoglobulin light chain, immunoglobulin light chain fragment, immunoglobulin heavy chain, and immunoglobulin heavy chain fragment.

In one embodiment of the polynucleotide, the nucleic acid encoding GAS1 has the sequence of SEQ ID NO: 3.

In another embodiment, the nucleic acid encoding GAS1 has the sequence of SEQ ID NO: 4.

In another embodiment of the polynucleotide, a host cell is disclosed, wherein the host cell is transformed with the polynucleotide of the invention.

In another embodiment, a bacteriophage is disclosed, wherein the bacteriophage comprising the polynucleotide molecule.

In another aspect, a polynucleotide molecule is disclosed, the polynucleotide comprising a dicistronic transcription unit comprising a nucleic acid encoding an immunoglobulin heavy chain variable domain and an immunoglobulin light chain variable domain, the 5' end of each of said immunoglobulin heavy and light chain variable domains being operably linked to the 3' end of a nucleic acid encoding a GAS1 secretion signal peptide.

In one embodiment of the polynucleotide, the nucleic acid encoding the GAS1 secretion signal peptide has the sequence of SEQ ID NO: 3.

In another embodiment, the nucleic acid encoding a GAS1 secretion signal peptide has the sequence of SEQ ID NO: 4.

In another embodiment, the dicistronic transcription unit is operably linked to a prokaryotic promoter sequence.

In another embodiment, a host cell is disclosed wherein the host cell is transformed with the polynucleotide molecule of the invention.

In another embodiment, a bacteriophage is disclosed wherein the bacteriophage comprises the polynucleotide molecule.

In another aspect, a polypeptide is disclosed, the polypeptide comprising a GAS1 secretion signal peptide linked to a single immunoglobulin variable domain polypeptide.

In one embodiment, the C-terminal end of said immunoglobulin variable domain polypeptide is in turn linked to a bacteriophage coat protein.

In another embodiment, the immunoglobulin variable domain polypeptide comprises a light chain variable domain ($V_L$).

In another embodiment, the immunoglobulin variable domain polypeptide comprises a heavy chain variable domain ($V_H$).

In yet another embodiment of the invention, a polypeptide library is disclosed the polypeptide library comprising a plurality of polypeptide molecules according to the invention.

In another embodiment, a host cell is disclosed the host cell comprising the polypeptide.

In another embodiment, a bacteriophage is disclosed the bacteriophage comprising the polypeptide.

In a further embodiment, the polypeptide is integrated into the bacteriophage coat.

In another embodiment of the polypeptide, the immunoglobulin variable domain polypeptide is operably linked at its N-terminus to a GAS1 secretion signal peptide.

In another embodiment of the polypeptide, the immunoglobulin variable domain polypeptide comprises an immunoglobulin heavy chain variable domain polypeptide linked at its N-terminus to the GAS1 secretion signal peptide.

In yet another embodiment of the polypeptide, the immunoglobulin variable domain polypeptide comprises an immunoglobulin light chain variable domain polypeptide linked at its N-terminus to the GAS1 secretion signal peptide.

In another embodiment, a bacteriophage is disclosed the bacteriophage comprising the immunoglobulin variable domain polypeptide.

In another aspect, a recombinant nucleic acid vector is disclosed the vector comprising a promoter operably linked to a nucleic acid sequence encoding a GAS1 secretion signal peptide, wherein said promoter is not a rhamnose promoter.

In yet another aspect of the invention, a recombinant nucleic acid vector is disclosed the vector comprising a promoter operably linked to a nucleic acid sequence encoding a GAS1 secretion signal peptide, which in turn is operably linked to a sequence encoding an immunoglobulin variable region polypeptide.

In another aspect of the invention, a method for selecting from a repertoire of polypeptides one or more immunoglobulin variable region polypeptides that bind to a target ligand is disclosed, the method comprising; expressing a polynucleotide library in a host cell to produce a polypeptide library, contacting the polypeptide library with a target ligand, and selecting one or more polypeptides which bind to the target ligand.

In another embodiment, the step of expressing comprises infecting the host cell comprising the library with bacteriophage. The polynucleotide molecules of the library are expressed by the bacteriophage.

In another embodiment, the step of contacting comprises contacting a bacteriophage, which expresses the library with the target ligand.

In another aspect, a method for selecting from a repertoire of polypeptides one or more immunoglobulin variable region polypeptides that bind to a target ligand, is disclosed, the method comprising, contacting the polypeptide library with a target ligand and selecting one or more polypeptides which bind to the target ligand.

In another aspect of the invention, a method of producing an immunoglobulin variable region polypeptide is disclosed. The method comprising culturing a host cell which has been transformed with a polynucleotide molecule encoding the immunoglobulin variable region polypeptide under conditions to express the immunoglobulin variable region polypeptide. The polynucleotide molecule comprises a first nucleic acid encoding a first GAS1 secretion signal peptide operably linked to a nucleic acid sequence encoding an immunoglobulin heavy chain variable region polypeptide; and a second nucleic acid encoding a second GAS1 secretion signal peptide operably linked to a nucleic acid sequence encoding an immunoglobulin light chain variable region polypeptide. The first and second nucleic acid sequences are operably linked to a single promoter so as to provide a dicistronic transcription unit. The final step comprises expressing and secreting the immunoglobulin variable region polypeptide.

In another embodiment of the method, the nucleic acid encoding a GAS1 secretion signal peptide is optimized for bacterial expression.

In another embodiment, the nucleic acid encoding a GAS1 secretion signal peptide has the sequence of SEQ ID NO: 3.

In another embodiment, the nucleic acid encoding a GAS1 secretion signal peptide has the sequence of SEQ ID NO: 4.

In another aspect, a method of producing an immunoglobulin heavy chain variable region polypeptide is disclosed, the method comprising culturing a host cell which has been transformed with a polynucleotide molecule encoding said immunoglobulin heavy chain variable region polypeptide under conditions to express said immunoglobulin heavy chain variable region polypeptide. The polynucleotide molecule comprises a nucleic acid encoding a GAS1 secretion signal peptide operably linked to an immunoglobulin heavy chain variable region polypeptide.

In another aspect, a method of producing an immunoglobulin light chain variable region polypeptide is disclosed the method comprising culturing a host cell which has been transformed with a polynucleotide molecule encoding said immunoglobulin light chain variable region polypeptide under conditions to express said immunoglobulin light chain variable region polypeptide. The polynucleotide molecule comprises a nucleic acid encoding a GAS1 secretion signal peptide operably linked to an immunoglobulin light chain variable region polypeptide.

In one embodiment the method of either of the two preceding aspects, the GAS1 secretion signal peptide is encoded by the nucleic acid sequence of SEQ ID NO: 3 or 4.

In another aspect a fusion protein is disclosed, the fusion protein comprising an immunoglobulin variable region polypeptide operably linked with a GAS1 secretion signal peptide.

In another aspect of the invention, a method of preparing a polypeptide library is disclosed, the method comprising introducing a polynucleotide, which polypeptide encodes an exogenous immunoglobulin variable region polypeptide, into the genome of a replicable genetic package, thus forming a fusion protein with an endogenous protein that is normally expressed from the outer surface of the replicable genetic package. The polynucleotide is operably linked to a polynucleotide encoding a GAS1 secretion signal sequence. Upon expression, the fusion protein is transported to the outer surface of the replicable genetic package, and assembled to display the exogenous immunoglobulin variable region polypeptide from the outer surface of the replicable genetic package.

In one embodiment of the method, the nucleic acid encoding a GAS1 secretion signal peptide has the sequence of SEQ ID NO: 3.

In another embodiment, the nucleic acid encoding a GAS1 secretion signal peptide has the sequence of SEQ ID NO: 4.

In another embodiment, the immunoglobulin variable domain polypeptide comprises a light chain variable domain ($V_L$).

In another embodiment, the immunoglobulin variable domain polypeptide comprises a heavy chain variable domain ($V_H$).

In another aspect, a method of identifying an antibody polypeptide that binds a desired target is disclosed, the method comprising introducing a polynucleotide library as recited herein above to a host cell, and selecting a member of the library that encodes a polypeptide which binds the target.

In a final aspect, a method of producing a member of a specific binding pair (sbp member) is disclosed, which sbp member is a human antibody polypeptide that binds a human self antigen, the method comprising: a) providing a library comprising filamentous bacteriophage that each display at their surface an sbp member, wherein each filamentous bacteriophage that displays at its surface an sbp member contains a nucleic acid with sequence that encodes a GAS1 secretion signal peptide operably linked to sequence which encodes that sbp member, wherein the sbp members displayed in the library are human antibody sequences obtained without immunizing a human with said human self-antigen and without obtaining nucleic acid from a human having an autoimmune disease involving an immune response to the human self antigen; and b) selecting one or more specific binding pair members with binding specificity for the target human self antigen, by binding with the target human self antigen one or more sbp members displayed at the surface of filamentous bacteriophage in the library.

In one embodiment, a method of producing a modified member of a specific binding pair identified according to the method described above is provided, the method comprising introducing one or more of an addition, deletion, substitution or insertion of one or more amino acids to the coding region of the nucleic acid encoding a member of an sbp identified as described above, or linkage of another molecule to the member of an sbp identified as described above, and binding the resulting polypeptide with the human self antigen.

BRIEF DESCRIPTION OF THE DRAWINGS

FIG. 1 shows a nucleotide sequence comparison of GAS1 secretion signal peptide variants. GAS wt: The naturally occurring sequence in yeast (SEQ ID NO: 1). The yeast wt leader peptide sequence is MLFKSLSKLATAAAFFAG-VATA (SEQ ID NO: 2). GAS leader *E. coli*: The nucleotide sequence according to optimal *E. coli* codon usage (Wada et al. 1992 *Nucleic Acids Research* 20:2111-2118) (SEQ ID NO: 3). GAS leader AT: AT rich nucleotide sequence (SEQ ID NO: 4). All nucleotide sequences encode the same amino acid sequence. Light gray indicates nucleotides that are similar for all sequences. Dark gray indicates nucleotides that are similar to the wt sequence. White indicates nucleotides that are different from the wt sequence.

FIG. 2 shows an expression vector map for the vector used to test signal peptides.

FIG. 3 shows the results of ELISA assays of the level of secretion of a HEL4 dAb expressed with different secretion signals.

FIG. 4 shows expression levels of dAb HEL4 with a GAS1 signal peptide as measured by SDS-PAGE. dAbs were purified from 50 ml culture supernatants using protein A Sepharose in a batch-wise manner. Purified dAbs were analyzed on a SDS PAGE. Lane 1: GAS AT rich signal peptide; Lane 2: gene3 signal peptide with N terminal FLAG tag. Expression levels were determined using OD280. Lane 1: GAS 32 mg/l; Lane 2: gene3 with FLAG tag 14.3 mg/l.

FIG. 5 shows the specific activity of dAb HEL4 with a GAS signal peptide. The data shown are a comparison of the binding of dAb HEL4 produced with GAS AT rich signal peptide versus gene3 signal peptide. Lysozyme was coated on an ELISA plate and binding dAbs were detected using the VSV tag. Indicated values are means of two independent measurements.

FIG. 6 shows a separate measurement of the specific activity of dAb HEL4 with a GAS signal peptide. The data shown are a comparison of the binding of dAb HEL4 produced with GAS AT rich signal peptide versus gene3 signal peptide. Lysozyme or anti-myc antibody was coated on an ELISA plate, and binding phage were detected using anti-M13 HRP conjugate antibody.

DETAILED DESCRIPTION

Definitions

Figure 7A:
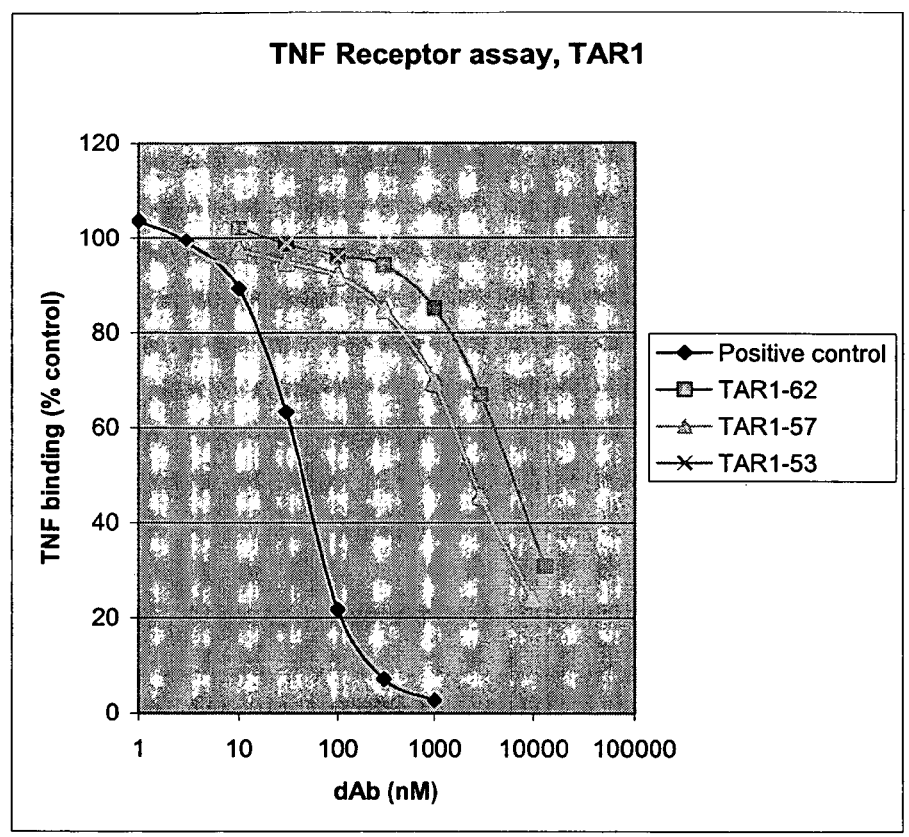
FIG. 7 shows that anti-TNF-α dAbs neutralize cytotoxic activity of TNF-α. (A) The isolated dAbs TAR1-53, 57 and 62 bind TNF-α specifically and block the binding of TNF-.alpha. to its receptor TNF R1 in a ELISA based receptor binding assay. (B) The dAbs TAR1-53, 57 and 62 block the cytotoxic activity of TNF-α on L929 cells.

As used herein "GAS1 secretion signal peptide" refers to the secretion signal peptide of the *S. cerevisiae* GAS1 surface glycoprotein (Nueoffer et al., 1990, Mol. Cell Biol., 11: 27-37). "GAS1 secretion signal peptide" as used herein refers to a secretion signal peptide having the sequence of SEQ ID NO: 2, and which is encoded by the polynucleotide sequence of SEQ ID NO: 1, as well has sequences which are at least 75%, 80%, 90%, and up to 99% identical with either the peptide sequence of SEQ ID NO: 2 or polynucleotide sequence of SEQ ID NO: 1. Identity refers to the optimal alignment of sequences (either nucleotides or amino acids), which may be conducted by computerized implementations of algorithms. Identity with regard to polynucleotides, for example, may be determined by analysis with BLASTN version 2.0 using the default parameters. Identity, with respect to polypeptides (i.e., amino acids), may be determined using a program, such as BLASTP version 2.2.2 with the default parameters, which aligns the polypeptides or fragments being compared and determines the extent of amino acid identity or similarity between them.

As used herein, a "GAS1 secretion signal peptide" also refers to a secretion signal peptide which is encoded by a GAS1 polynucleotide sequence which has been optimized for expression in bacteria. "Optimized" as used herein refers to the modification of the codon of a polynucleotide sequence to a codon sequence which is expressed in bacteria such as *E. coli* at a level which is at least 10%, 20%, 30%, 50%, 70%, 80% and up to 100% greater than a non-optimized sequence. An "A/T optimized" nucleic acid sequence according to one aspect of the invention is a sequence in which G or C nucleotides are mutated to an A or T nucleotide, provided that the mutation does not change the amino acid encoded by the codon. If neither an A or T nucleotide can be substituted for a G or C nucleotide in a sequence without changing the amino acid, the G or C nucleotide is not mutated to an A or T nucleotide. An "optimized" nucleic acid sequence encoding a GAS1 secretion signal peptide according to the invention is preferably SEQ ID Nos. 3 or 4.

As used herein, the term "immunoglobulin variable region polypeptide" includes i) an antibody heavy chain variable domain ($V_H$), or antigen binding fragment thereof, with or without constant region domains ii) an antibody light chain variable domain ($V_L$), or antigen binding fragment thereof, with or without constant region domains iii) a $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$), and iv) single-chain Fv antibodies (scFv) that is a $V_L$ domain polypeptide without constant regions linked to another $V_H$ domain polypeptide without constant regions ($V_H$-$V_L$), the variable domains together forming an antigen binding site. In one embodiment of option (i), (ii), or (iii), each variable domain forms and antigen binding site independently of any other variable domain. Option (i) or (ii) can be used to form a Fab fragment antibody or an Fv antibody. Thus, as used herein, the term "immunoglobulin variable region polypeptide" refers to antibodies that may or may not contain constant region domains. In addition, as used herein, the term "immunoglobulin variable region polypeptide" refers to antigen binding antibody fragments that can contain either all or just a portion of the corresponding heavy or light chain constant regions. In addition, an "immunoglobulin variable region polypeptide", as used herein includes light chain, heavy chain, heavy and light chains (e.g., scFv), Fd (i.e., $V_H$-$C_H$1) or $V_L$-$C_L$. An "immunoglobulin variable region polypeptide" as used herein, does not refer to a whole antibody molecule (e.g., IgG) comprising two heavy and two light chains. A "whole antibody" as used herein refers to an antibody molecule in which two heavy chains are each disulfide bonded to a light chain, and where the two heavy chains are disulfide bonded at the hinge region to each other.

As used herein, the term "domain" refers to a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain.

The equivalent terms "single variable domain antibody" and "single immunoglobulin variable domain" refer to a folded polypeptide domain which comprises sequences characteristic of immunoglobulin variable domains and which specifically binds an antigen (i.e., dissociation constant of 500 nM or less), and which binds antigen as a single variable domain; that is, without any complementary variable domain. A "single variable domain antibody" therefore includes complete antibody variable domains as well as modified variable domains, for example in which one or more loops have been replaced by sequences which are not characteristic of antibody variable domains or antibody variable domains which have been truncated or comprise N- or C-terminal extensions, as well as folded fragments of variable domains which retain a dissociation constant of 500 nM or less (e.g., 450 nM or less, 400 nM or less, 350 nM or less, 300 nM or less, 250 nM or less, 200 nM or less, 150 nM or less, 100 nM or less) and the target antigen specificity of the full-length domain. Preferably an antibody single variable domain useful in the invention is selected from the group of $V_H$ and $V_L$, including $V_{kappa}$ and $V_{lambda}$.

The phrases "single variable domain antibody" and "single immunoglobulin variable domain" encompass not only an isolated antibody single variable domain polypeptide, but also larger polypeptides that comprise one or more monomers of an antibody single variable domain polypeptide sequence. A "domain antibody" or "dAb" is equivalent to an "antibody single variable domain" polypeptide as the term is used herein. An antibody single variable domain polypeptide, as used herein refers to a mammalian single immunoglobulin variable domain polypeptide, preferably human, but also includes rodent or camelid dAbs.

As used herein, "library" refers to a mixture of heterogeneous polypeptides or nucleic acids containing in the range of $10$-$10^{12}$ (e.g., $10^9$ to $10^{12}$) different members. Each member comprises one polypeptide or nucleic acid sequence variant of an immunoglobulin variable region. To this extent, library is synonymous with repertoire. Sequence differences between library members are responsible for the diversity present in the library. A "library" may refer to a simple mixture of polypeptides or nucleic acids, or may be organisms or cells, for example bacteria, viruses, animal or plant cells and the like, transformed with a library of nucleic acids. Preferably, each individual organism, virus, or cell contains only one member of the library. Advantageously, the nucleic acids are incorporated into expression vectors, in order to allow expression of the polypeptides encoded by the nucleic acids. In a preferred aspect, therefore, a "library" refers to a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

As used herein, a "replicable genetic package" refers to an entity which combines phenotype and genotype of members of a library of (poly)peptides/proteins by linking the genetic information encoding the library member and the (poly)peptide/protein expressed therefrom. The library can be screened and/or selected for a desired property, and the (poly)peptide/protein being screened and/or selected can be identified via the genetic information associated with the same. Examples for "replicable genetic packages" comprise cells, such as bacteria (WO 90/02809; Georgiou et al., 1993; Francisco & Georgiou, 1994; Daugherty et al., 1998), yeast (Boder & Wittrup, 1997; Kieke et al., 1997; Cho et al., 1998; Kieke et al., 1999) insect cells (Ernst et al., 1998), viruses, such as bacteriophage (WO 90/02809; Kay et al., 1996; Dunn, 1996; McGregor, 1996) retroviruses (Russell et al., 1993), spores (WO 90/02809), or complexes of nucleic acid molecules and (poly)peptides/proteins expressed therefrom, such as in ribosome complexes (Hanes & Pluckthun, 1997; Hanes et al., 1998; Hanes et al., 1999) or in complexes connected either non-covalently (Cull et al., 1992; Schatz, 1993; Schatz et al., 1996; Gates et al., 1996) or covalently (Nemoto et al., 1997).

As used herein, "secretable" refers to the ability of polypeptides to be extracellularly secreted after their synthesis within cells. For example, polypeptides comprising the GAS1 secretion signal peptide are able to be secrete the polypeptide into the periplasm of gram negative *E. coli*. A "secretable" or "secreted" polypeptide either accumulates in the periplasmic space of, for example, a bacterial host, or accumulates in the growth medium. Methods of determining whether a polypeptide, e.g., a single domain antibody, is "secretable" or "secreted" include, for example, ELISA, as taught in Example 2, western blot, and purification of culture supernatants using protein A Sepharose, with subsequent and visualization on SDS PAGE as taught in Example 3. In a preferred embodiment, "secretable" polypeptides can permeate cell membranes such that the product accumulates to between 100 μg/ml and 1 g/l, e.g., 1 mg/l to 1 g/l, 1 mg/l to 50 mg/l, 1 mg/l to 100 mg/l, 1 mg/l to 150 mg/l, 1 mg/l to 200 mg/l, 1 mg/l to 250 mg/l, 1 mg/l to 300 mg/l, 1 mg/l to 350 mg/l, 1 mg/l to 400 mg/l, 1 mg/l to 450 mg/l, 1 mg/l to 500 mg/l, 1 mg/l to 550 mg/l, 1 mg/l to 600 mg/l, 1 mg/l to 650 mg/l, 1 mg/l to 700 mg/l, 1 mg/l to 750 mg/l, 1 mg/l to 800 mg/l, 1 mg/l to 850 mg/l, 1 mg/l to 900 mg/l, 1 mg/l to 950 mg/l, in the culture supernatant.

As used herein, "bacteriophage coat protein" refers to the bacteriophage proteins that provide the structure of bacteriophage particles. Non-limiting examples of bacteriophage coat proteins include, without limitation, M13 gene III, gene VIII; rd minor coat protein pIII (Saggio et al., *Gene* 152:35, 1995); lambda D protein (Stemberg & Hoess, *Proc. Natl. Acad. Sci. USA* 92:1609, 1995; Mikawa et al., *J. Mol Biol.* 262:21, 1996); lambda phage tail protein pV (Maruyama et al., *Proc. Natl. Acad. Sci. USA* 91:8273, 1994; U.S. Pat. No. 5,627,024); fr coat protein (WO96/11947; DD 292928; DD 286817; DD 300652); Φ29 tail protein gp9 (Lee, *Virol.* 69:5018, 1995); MS2 coat protein; T4 small outer capsid protein (Ren et al., *Protein Sci.* 5:1833, 1996), T4 nonessential capsid scaffold protein IPIII (Hong and Black, *Virology* 194:481, 1993), or T4 lengthened fibritin protein gene (Efimov, *Virus Genes* 10:173, 1995); PRD-1 gene III; Qβ3 capsid protein (as long as dimerization is not interfered with); and P22 tailspike protein (Carbonell and Villaverde, *Gene* 176: 225, 1996).

As used herein, a "dicistronic transcription unit" refers to a nucleic acid sequence that allows the coexpression of more than one open reading frame from a single promoter. A "transcription unit" is a nucleic acid containing a gene coding for a desired protein, under the control of a suitable promoter and having all the essential functions to enable expression. The "dicistonic transcription unit" is a transcription unit in which two genes are under control of the same promoter. For additional information on "dicistronic transcription unit" see Dirks, et al., Gene, vol. 128, pp. 247-249 (1993), herein incorporated by reference.

The present invention provides a GAS1 secretion signal polypeptide suitable for efficient expression in different vectors and both prokaryotic and eukaryotic organisms. Also provided is a secretion signal peptide that permits easy shuttle between phage, bacteria, yeast and mammalian cells. Thus, in one aspect, the invention relates to polynucleotide molecules comprising a promoter operably linked to a nucleic acid sequence encoding a Glycophospolipid-Anchored Surface protein, herein referred to as GAS 1, secretion signal peptide. In some embodiments the promoter is not a rhamnose promoter. In some embodiments the invention relates to a polynucleotide comprising a GAS1 secretion signal polypeptide which is operably linked to a nucleic acid encoding an immunoglobulin variable region domain polypeptide. In a further embodiment the invention relates to a polynucleotide comprising a GAS1 secretion signal polypeptide which is operably linked to a single domain antibody.

According to the invention, GAS1 secretion signal peptides include those peptides encoded by the wild type nucleic acid GAS1 sequence found in *Saccharomyces cerevisiae* and herein taught in SEQ ID NO:1.

Preparing GAS1 AT Rich Nucleotide Sequences

Cloned wild type (SEQ ID NO: 1) GAS 1 secretion signal peptide nucleic acids can be mutated to generate GAS1 secretion signal AT rich nucleic acids (SEQ ID NOs:3 and 4). AT-rich nucleic acids of the present invention allow for optimized expression in *E. coli*. The signal peptide coding regions were optimized according to *E. coli* codon usage using Vector NTI v. 7 (INVITROGEN™) as described in Example 2. Furthermore, codon usage at the 5' of the mRNA is important for optimal expression of the protein (Tessler, et al. *NAR.* 12:7663; Wood, et al. *NAR.* 20: 2111). In order to encode the best GAS1 secretion signal peptide, A/T rich sequences are favored (Humphreys, et al. 2000, *Protein Expression and Purification* 20:252, herein incorporated by reference). Each guanine or cytosine was changed to an adenine or a thymine, if it did not result in an amino acid change.

The methods to create AT rich GAS1 secretion signal peptides are taught below and other methods are known in the art. The wild type GAS1 secretion signal nucleic acid sequence can be used to prepare the GAS1 AT rich nucleic acids.

In one aspect, an AT rich GAS1 secretion signal peptide can be prepared by genetic modification (e.g., by modifying the DNA sequence encoding a wild type GAS1 secretion signal peptide). A number of methods are known in the art that permit targeted mutation of DNA sequences (see for example, Ausubel et. al. *Short Protocols in Molecular Biology* (1995) 3*rd* Ed. John Wiley & Sons, Inc.).

There are a number of site-directed mutagenesis methods known in the art which allow one to mutate a particular site or region in a straightforward manner. There are a number of kits available commercially for the performance of site-directed mutagenesis, including both conventional and PCR-based methods. Useful examples include the EXSITE™ PCR-Based Site-directed Mutagenesis Kit available from Stratagene (Catalog No. 200502; PCR based) and the QUIKCHANGE™ Site-directed mutagenesis Kit from Stratagene (Catalog No. 200518; non-PCR-based), and the CHAMELEON® double-stranded Site-directed mutagenesis kit, also from Stratagene (Catalog No. 200509).

Older methods of site-directed mutagenesis known in the art relied upon sub-cloning of the sequence to be mutated into a vector, such as an M13 bacteriophage vector, that allows the isolation of single-stranded DNA template. In these methods one annealed a mutagenic primer (i.e., a primer capable of annealing to the site to be mutated but bearing one or mismatched nucleotides at the site to be mutated) to the single-stranded template and then polymerized the complement of the template starting from the 3' end of the mutagenic primer. The resulting duplexes were then transformed into host bacteria and plaques were screened for the desired mutation.

More recently, site-directed mutagenesis has employed PCR methodologies, which have the advantage of not requiring a single-stranded template. In addition, methods have been developed that do not require sub-cloning. Several issues may be considered when PCR-based site-directed mutagenesis is performed. First, in these methods it may be desirable to reduce the number of PCR cycles to prevent expansion of undesired mutations introduced by the polymerase. Second, a selection may be employed in order to reduce the number of non-mutated parental molecules persisting in the reaction. Third, an extended-length PCR method may be preferred in order to allow the use of a single PCR primer set. And fourth, because of the non-template-dependent terminal extension activity of some thermostable polymerases it may be necessary to incorporate an end-polishing step into the procedure prior to blunt-end ligation of the PCR-generated mutant product.

In some embodiments, a wild-type GAS1 secretion signal is cloned by isolating genomic or cDNA, using molecular biological methods, to serve as a template for mutagenesis. Alternatively, the genomic DNA or cDNA may be amplified by PCR and the PCR product may be used as template for mutagenesis.

The non-limiting protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease DpnI (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

One method is described in detail as follows for PCR-based site directed mutagenesis according to one embodiment of the invention.

Plasmid template DNA comprising a GAS1 secretion signal polynucleotide (approximately 0.5 pmole) is added to a PCR cocktail containing: 1× mutagenesis buffer (20 mM Tris HCl, pH 7.5; 8 mM MgCl$_2$; 40 µg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation within the DNA polymerase encoding sequence, and one (the same or the other) must contain a 5' phosphate to facilitate later ligation), 250 uM each dNTP, 2.5 U Taq DNA polymerase, and 2.5 U of Taq Extender (Available from Stratagene; See Nielson et al. (1994) Strategies 7: 27, and U.S. Pat. No. 5,556,772).

Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5 U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 µl of 1×) containing 0.5 mM ATP is added to the DpnI-digested, Pfu DNA polymerase-polished PCR products. The solution is mixed and 10 µl are removed to a new microfuge tube and T4 DNA ligase (2-4 U) is added. The ligation is incubated for greater than 60 min at 37° C. Finally, the treated solution is transformed into competent *E. coli* according to standard methods.

A degenerate oligonucleotide primer may be used for generating GAS1 AT enriched secretion signal nucleotides of the present invention. In some embodiments, chemical synthesis of a degenerate primer is carried out in an automatic DNA synthesizer, and the purpose of a degenerate primer is to provide, in one mixture, all of the sequences encoding a specific desired mutation site of the DNA polymerase sequence. The synthesis of degenerate oligonucleotides is well known in the art (e.g., Narang, S. A, Tetrahedron 39:3 9, 1983; Itakura et al., Recombinant DNA, Proc 3rd Cleveland Sympos. Macromol., Walton, ed., Elsevier, Amsterdam, pp 273-289, 1981; Itakura et al., Annu. Rev. Biochem. 53:323, 1984; Itakura et al., Science 198:1056, 1984; and Ike et al., Nucleic Acid Res. 11:477 1983). Such techniques have been employed in the directed evolution of other proteins (e.g., Scott et al., Science 249:386-390, 1980; Roberts et al., Proc. Nat'l. Acad. Sci., 89:2429-2433, 1992; Devlin et al., Science 249: 404-406, 1990; Cwirla et al., Proc. Nat'l. Acad. Sci., 87: 6378-6382, 1990; as well as U.S. Pat. Nos. 5,223,409, 5,198, 346, and 5,096,815, each of which is incorporated herein by reference).

Polynucleotides encoding the desired AT enriched GAS1 signal peptides generated by mutagenesis may be sequenced to identify the mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

In a preferred embodiment, the AT enriched GAS1 signal peptide is derived from an *S. cervisiae* (SEQ ID NO:1)

In a preferred embodiment, the AT enriched GAS1 signal peptide is encoded by the nucleic acid of SEQ ID NO:3 or 4.

A detailed description of the S. cervisiae cloning of the GAS1 protein can be fund in Nuoffer et al. Molecular and Cellular Biology; 11:27 (1991), herein incorporated by reference.

A person of ordinary skill in the art having the benefit of this disclosure will recognize that GAS1 secretion signal peptides and the like may be suitably used in the present invention.

Bacteriophage Coat Proteins:

In the present invention, a variety of bacteriophage systems and bacteriophage coat proteins can be used. Examples of suitable bacteriophage coat proteins include, without limitation, M13 gene III, gene VIII; rd minor coat protein pIII (Saggio et al., *Gene* 152:35, 1995); lambda D protein (Stemberg & Hoess, *Proc. Natl. Acad. Sci. USA* 92:1609, 1995; Mikawa et al., *J. Mol Biol.* 262:21, 1996); lambda phage tail protein pV (Maruyama et al., *Proc. Natl. Acad. Sci. USA* 91:8273, 1994; U.S. Pat. No. 5,627,024); fr coat protein (WO96/11947; DD 292928; DD 286817; DD 300652); Φ29 tail protein gp9 (Lee, *Virol.* 69:5018, 1995); MS2 coat protein; T4 small outer capsid protein (Ren et al., *Protein Sci.* 5:1833, 1996), T4 nonessential capsid scaffold protein IPIII (Hong and Black, *Virology* 194:481, 1993), or T4 lengthened fibritin protein gene (Efimov, *Virus Genes* 10:173, 1995); PRD-1 gene III; Qβ3 capsid protein (as long as dimerization is not interfered with); and P22 tailspike protein (Carbonell and Villaverde, *Gene* 176:225, 1996). Techniques for inserting foreign coding sequence into a phage gene are well known (see e.g., Sambrook et al., *Molecular Cloning: A Laboratory Approach*, Cold Spring Harbor Press, New York, 1989; Ausubel et al., *Current Protocols in Molecular Biology*, Greene Publishing Co., New York, 1995).

In a preferred aspect, a filamentous bacteriophage coat protein is used. Many filamentous bacteriophage vectors are commercially available that can allow for the in-frame ligation of the signal peptide-tag-immunoglobulin variable region polypeptide fusion protein to a bacteriophage coat protein. The most common vectors accept DNA inserts for in frame fusions with gene III or gene VIII. Non-limiting examples of suitable vectors include, M13 mp vectors (Pharmacia Biotech), pCANTAB 5e (Pharmacia Biotech), pCOMB3 and M13KE (New England Biolabs), pBluescript series (Stratagene Cloning Systems, La Jolla, Calif.). It should be understood that these vectors already contain bacteriophage signal peptide sequences and that each vector can be modified to contain the bacteriophage signal peptide sequence of interest by methods well known in the art (Sambrook et al., *Molecular Biology: A laboratory Approach*, Cold Spring Harbor, New York 1989; Ausubel, et al., *Current protocols in Molecular Biology*, Greene Publishing, New York, 1995.

Vectors:

The present invention encompasses polynucleotide molecules which are cloned into a vector such that the polynucleotide molecule is functionally linked to a promoter that is functional in a prokaryote and to a GAS1 secretion signal peptide.

For the aspects described herein, both phagemid and nonphagemid vectors can be used. As used herein, vector refers to a discrete element that is used to introduce heterologous DNA into cells for the expression and/or replication thereof. Methods by which to select or construct and, subsequently, use such vectors are well known to one of skill in the art. Numerous vectors are publicly available, including bacterial plasmids, bacteriophage, artificial chromosomes, episomal vectors and gene expression vectors can be employed. A vector of use according to the invention may be selected to accommodate a polypeptide coding sequence of a desired size. A suitable host cell is transformed with the vector after in vitro cloning manipulations. Host cells may be prokaryotic, such as any of a number of bacterial strains, or may be eukaryotic, such as yeast or other fungal cells, insect or amphibian cells, or mammalian cells including, for example, rodent, simian or human cells. Each vector contains various functional components, which generally include a cloning (or "polylinker") site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. For example, the origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector can contain a selection gene also referred to as a selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since the replication of vectors according to the present invention is most conveniently performed in *E. coli* (e.g., strain TB1 or TG1), an *E. coli*-selectable marker, for example, the β-lactamase gene that confers resistance to the antibiotic ampicillin, is of use. These can be obtained from *E. coli* plasmids, such as pBR322 or a pUC plasmid such as pUC18 or pUC19, or pUC119.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), pGEM1 (Promega Biotec, Madison, Wis., USA) pQE70, pQE60, pQE-9 (Qiagen), pD10, phiX174, pBluescript™ II KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector can be used as long as it is replicable and stable in the host cell.

The host cell can be any of the host cells familiar to those skilled in the art, including prokaryotic cells or eukaryotic cells. As representative examples of appropriate hosts, there may be mentioned: bacteria cells, such as *E. coli, Streptomyces lividans, Streptomyces griseofuscus, Streptomyces ambo-*

*faciens, Bacillus subtilis, Salmonella typhimurium* and various species within the genera *Pseudomonas, Streptomyces, Bacillus*, and *Staphylococcus*, fungal cells, such as yeast, insect cells such as *Drosophila S2* and *Spodoptera Sf9*, animal cells such as CHO, COS or Bowes melanoma, and adenoviruses. The selection of an appropriate host is within the abilities of those skilled in the art.

Expression vectors usually contain a promoter that is recognized by the host organism and is operably linked to the coding sequence of interest. Such a promoter can be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. In addition, promoters can include, for example, the lambda phage $P_R$ or $P_L$ promoters, bacteriophage T7, T3, Sp6 promoters, *B. subtilis* alkaline protease promoter, and the *B. stearothermophilus* maltogenic amylase promoter, etc. Promoters for use in bacterial systems will also generally contain a Shine-Delgarno sequence operably linked to the coding sequence.

For promoters functional in eukaryotic systems, there are, for example, yeast promoters, such as GAL1, GAL4 and other glycolytic gene promoters (see for example, Hitzeman et al., 1980, J. Biol. Chem. 255: 12073-12080; Alber & Kawasaki, 1982, J. Mol. Appl. Gen. 1: 419-434), LEU2 promoter (Martinez-Garcia et al., 1989, Mol. Gen. Genet. 217: 464-470), alcohol dehydrogenase gene promoters (Young et al., 1982, in Genetic Engineering of Microorganisms for Chemicals, Hollaender et al., eds., Plenum Press, New York), or the TPI1 promoter (U.S. Pat. No. 4,599,311); insect promoters, such as the polyhedrin promoter (U.S. Pat. No. 4,745,051; Vasuvedan et al., 1992, FEBS Lett. 311: 7-11), the P10 promoter (Vlak et al., 1988, J. Gen. Virol. 69: 765-776), the Autographa californica polyhedrosis virus basic protein promoter (EP 397485), the baculovirus immediate-early gene promoter gene 1 promoter (U.S. Pat. Nos. 5,155,037 and 5,162,222), the baculovirus 39K delayed-early gene promoter (also U.S. Pat. Nos. 5,155,037 and 5,162,222) and the OpMNPV immediate early promoter 2; mammalian promoters—the SV40 promoter (Subramani et al., 1981, Mol. Cell. Biol. 1: 854-864), metallothionein promoter (MT-1; Palmiter et al., 1983, Science 222: 809-814), adenovirus 2 major late promoter (Yu et al., 1984, Nucl. Acids Res. 12: 9309-21), and cytomegalovirus (CMV) promoter (Tong et al., 1998, Anticancer Res. 18: 719-725), among others.

A selected promoter functional in eukaryotic or prokaryotic cells can also be linked to sequences rendering it inducible or tissue-specific. For example, the addition of a tissue-specific enhancer element upstream of a selected promoter may render the promoter more active in a given tissue or cell type. Alternatively, or in addition, inducible expression may be achieved by linking the promoter to any of a number of sequence elements permitting induction by, for example, thermal changes (temperature sensitive), chemical treatment (for example, metal ion- or IPTG-inducible), or the addition of an antibiotic or other inducing agent (for example, tetracycline).

In a preferred aspect, a filamentous bacteriophage vector system is used for expression of the polypeptide fusion protein, such that the proteins are incorporated into bacteriophage for display on the outer surface of the bacteriophage particle. Many filamentous bacteriophage vectors (phage vectors) are commercially available for use that allow for the in-frame ligation of the DNA encoding the immunoglobulin variable region polypeptide fusion protein to a bacteriophage coat protein. The most common vectors accept DNA inserts for in frame fusions with M13 bacteriophage gene III or gene VIII bacteriophage coat proteins, as noted above. Non-limiting examples of suitable bacteriophage vectors include, M13 mp vectors (Pharmacia Biotech), pCANTAB 5e (Pharmacia Biotech), pCOMB3 and M13KE (New England Biolabs), and others as described in WO 00/29555, herein incorporated by reference. It should be understood that these vectors already contain bacteriophage secretion signal peptide sequences and that each such vector can be modified to contain the GAS1 secretion signal peptide sequence by methods well known in the art (Sambrook et al., *Molecular Biology: A laboratory Approach*, Cold Spring Harbor, N.Y. 1989; Ausubel, et al., *Current protocols in Molecular Biology*, Greene Publishing, Y, 1995).

In one aspect, there is a restriction enzyme recognition site interposed between the nucleic acid sequence encoding a GAS1 secretion signal peptide and the sequence encoding a polypeptide of interest, e.g., an antibody polypeptide. Restriction endonucleases and their recognition sites are well known to those of skill in the art. A wide variety of restriction endonucleases, recognizing a variety of different restriction sites, is described in, for example, the New England Biolabs catalog, the 2004 edition of which is incorporated herein by reference.

In another aspect, a nucleic acid construct as described herein comprises a dicistronic gene arrangement—i.e., an arrangement in which a single mRNA molecule encodes two separate polypeptides in two separate coding regions. The preferred discistronic gene arrangement comprises nucleic acid encoding an immunoglobulin heavy chain variable domain and an immunoglobulin light chain variable domain, each of which domains is operably linked at its 5' end to the 3' end of a GAS1 secretion signal peptide. While relatively uncommon in eukaryotic systems, dicistronic coding arrangements are common in prokaryotic systems. The preparation of a dicistronic construct is straightforward once one has the individual coding sequences in hand, requiring only standard cloning techniques. Thus, an order of sequences for a dicistronic construct as disclosed herein is as follows: promoter-signal sequence-polypeptide 1-signal sequence-polypeptide 2. As noted, it is preferred that both signal sequences are a GAS1 signal sequence, although another signal sequence can be used for one of the signal sequences if desired. In an alternative arrangement, the second signal sequence is internal to the second polypeptide sequence.

Construction of Libraries:

One aspect involves the generation of nucleic acid and polypeptide libraries containing diverse polypeptides expressed as fusions of a GAS1 secretion signal sequence as described herein. As used herein, the term "library" refers to a mixture of heterogeneous polypeptides or nucleic acids. The library is composed of members, a plurality of which has a unique polypeptide or nucleic acid sequence. To this extent, library is synonymous with repertoire. Sequence differences between library members are responsible for the diversity present in the library. The library can take the form of a simple mixture of polypeptides or nucleic acids, or can be in the form organisms or cells, for example bacteria, viruses, animal or plant cells and the like, transformed with a library of nucleic acids. Typically, each individual organism or cell contains only one member of the library. In certain applications, each individual organism or cell can contain two or more members of the library. Advantageously, the nucleic acids are incorporated into expression vectors, in order to allow expression of the polypeptides encoded by the nucleic acids. In a preferred aspect, therefore, a library can take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

Of particular use in the construction of libraries of the invention are selection display systems, which enable a nucleic acid to be linked to the polypeptide it expresses. As used herein, a selection display system is a system that permits the selection, by suitable display means, of the individual members of the library.

Any selection display system can be used in conjunction with a library as described herein. For example, polypeptide fusion proteins as described herein can be displayed on lambda phage capsids (phage bodies). Preferred selection systems of the invention are the filamentous bacteriophage systems. Selection protocols for isolating desired members of large libraries are known in the art, as typified by phage display techniques. An advantage of phage-based display systems is that, because they are biological systems, selected library members can be amplified simply by growing the phage containing the selected library member in bacterial cells. Furthermore, because the nucleotide sequence that encodes the polypeptide library member is contained on a phage or phage vector, sequencing, expression and subsequent genetic manipulation is relatively straightforward.

Methods for the construction of bacteriophage antibody display libraries and lambda phage expression libraries are well known in the art (McCafferty et al., Nature, 348:552-554, 1990; Kang et al., Proc. Natl. Acad. Sci. USA, 88:11120-11123, 1991; Clackson et al., Nature, 352:624-628, 1991; Lowman et al., Biochemistry, 30:10832-10838, 1991; Burton et al., Proc. Natl. Acad. Sci. USA, 88:10134-10137, 1991; Hoogenboom et al., Nucleic Acid Res., 19:4133-4137, 1991; Chang et al., J. Immunol., 147:3610-3614, 1991; Breitling et al., Gene, 104:147-153, 1991; Marks et al., J. Biol. Chem., 267:16007-16010, 1991; Barbas et al., Proc. Natl. Acad. Sci. USA, 89:10164-10168, 1992; Hawkins & Winter, Eur. J. Immunol., 22:867-870, 1992; Marks et al., J. Biol. Chem., 267:16007-16010, 1992; Lerner et al., Science, 258:1313-1314, 1992, incorporated herein by reference). In brief, the nucleic acids encoding the immunoglobulin variable region polypeptide fusion proteins are cloned into a phage vector that comprises a bacteriophage packaging signal and a gene encoding at least one bacteriophage coat protein as described herein or as known in the art, which allows for the incorporation of the nucleic acid into a phage particle.

Other systems for generating libraries of polypeptides or polynucleotides involve the use of cell-free enzymatic machinery for the in vitro synthesis of the library members. For example, in vitro translation can be used to synthesize polypeptides as a method for generating large libraries. These methods are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax), use the polysomes to display polypeptides for selection. These and all the foregoing documents are incorporated herein by reference.

Methods of generating diverse libraries of polypeptide fusion proteins are well known in the art. For example, U.S. Pat. No. 6,696,245, incorporated herein by reference, describes the generation of diverse libraries of antibody polypeptides. The methods described therein generally involve the randomization of selected regions of immunoglobulin gene coding regions, in particular $V_H$ and $V_L$ coding regions, while leaving other regions non-randomized. The '245 patent also describes the generation of scFv constructs comprising individually randomized $V_H$ and $V_L$ domains.

Immunoglobulin variable domain libraries can advantageously be designed to be based on a predetermined main chain conformation. Such libraries may be constructed as described in International Patent Application WO 99/20749, the contents of which are incorporated herein by reference. Thus, in one aspect, an immunoglobulin variable domain polypeptide or single-domain antibody fused to a GAS1 secretion signal peptide comprises an antibody heavy chain variable region polypeptide or single-domain antibody comprising an antibody heavy chain variable domain ($V_H$), or antigen binding fragment thereof, which comprises the amino acid sequence of germline $V_H$ segment DP-47. In another aspect, an immunoglobulin variable region polypeptide or single-domain antibody fused to a GAS1 secretion signal polypeptide comprises an antibody light chain variable domain ($V_L$), or antigen binding fragment thereof, which comprises the amino acid sequence of germline $V_\kappa$ segment DPK9. Such variable region polypeptides can be used for the production of scFvs or Fabs, e.g., an scFv or Fab comprising (i) an antibody heavy chain variable domain ($V_H$), or antigen binding fragment thereof, which comprises the amino acid sequence of germline $V_H$ segment DP-47 and (ii) an antibody light chain variable domain ($V_L$), or antigen binding fragment thereof, which comprises the amino acid sequence of germline $V_\kappa$ segment DPK9.

Introduction of Vectors to Host Cells:

Vector constructs or libraries of vector constructs containing polynucleotide molecules as described herein can be introduced to selected host cells by any of a number of suitable methods known to those skilled in the art. For example, vector constructs may be introduced to appropriate bacterial cells by infection, in the case of bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, Molecular Cloning, A Laboratory Manual, Cold Spring Harbor Laboratory Press, Cold Spring Harbor, N.Y.), but electroporation may also be used (Ausubel et al., 1988, Current Protocols in Molecular Biology, (John Wiley & Sons, Inc., NY, N.Y.)).

For the introduction of vector constructs to yeast or other fungal cells, chemical transformation methods are generally used (e.g. as described by Rose et al., 1990, Methods in Yeast Genetics, Cold Spring Harbor Laboratory Press, Cold Spring Harbor, N.Y.). For transformation of S. cerevisiae, for example, the cells are treated with lithium acetate to achieve transformation efficiencies of approximately $10^4$ colony-forming units (transformed cells)/μg of DNA. Transformed cells are then isolated on selective media appropriate to the selectable marker used. Alternatively, or in addition, where the vector encodes GFP as a marker, plates or filters lifted from plates may be scanned for GFP fluorescence to identify transformed clones.

For the introduction of vectors to mammalian cells, the method used will depend upon the form of the vector. Plasmid vectors may be introduced by any of a number of transfection methods, including, for example, lipid-mediated transfection ("lipofection"), DEAE-dextran-mediated transfection, electroporation or calcium phosphate precipitation. These methods are detailed, for example, in Current Protocols in Molecular Biology (Ausubel et al., 1988, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or Lipo-Taxi™(Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

Antibody Polypeptides:

In one aspect, as noted above, the polynucleotide molecule linked to a GAS1 secretion signal peptide-encoding sequence encodes an antibody polypeptide. Conventional antibodies are large multi-subunit protein molecules comprising at least four polypeptide chains. For example, human IgG has two heavy chains and two light chains that are disulfide bonded to form the functional antibody. The size of a conventional IgG is about 150 kD. While conventional antibodies are very useful, considerable efforts have focused on identifying and producing smaller antibody fragments that retain antigen binding function and solubility.

The heavy and light polypeptide chains of antibodies comprise variable (V) regions that directly participate in antigen interactions, and constant (C) regions that provide structural support and function in non-antigen-specific interactions with immune effectors. The antigen binding domain of a conventional antibody is comprised of two separate domains: a heavy chain variable domain ($V_H$) and a light chain variable domain ($V_L$: which can be either $V_\kappa$ or $V_\lambda$). The antigen binding site itself is formed by six polypeptide loops: three from the $V_H$ domain (H1, H2 and H3) and three from the $V_L$ domain (L1, L2 and L3). In vivo, a diverse primary repertoire of V genes that encode the $V_H$ and $V_L$ domains is produced by the combinatorial rearrangement of gene segments. C regions include the light chain C regions (referred to as $C_L$ regions) and the heavy chain C regions (referred to as $C_H1$, $C_H2$ and $C_H3$ regions).

A number of smaller antigen binding fragments of naturally occurring antibodies have been identified following protease digestion. These include, for example, the "Fab fragment" ($V_L$-$C_L$-$C_H1$-$V_H$), "Fab' fragment" (a Fab with the heavy chain hinge region) and "F(ab')$_2$ fragment" (a dimer of Fab' fragments joined by the heavy chain hinge region). Recombinant methods have been used to generate even smaller antigen-binding fragments, referred to as "single chain Fv" (variable fragment) or "scFv," consisting of $V_L$ and $V_H$ joined by a synthetic peptide linker.

Phage display technology (see, e.g., Smith, 1985, Science 228: 1315; Scott & Smith, 1990, Science 249: 386; McCafferty et al., 1990, Nature 348: 552) provides an approach for the selection of antibody polypeptides which bind a desired target from among large, diverse repertoires of antibody polypeptides. These phage-antibody libraries can be grouped into two categories: natural libraries which use rearranged V genes harvested from human B cells (Marks et al., 1991, J. Mol. Biol., 222: 581; Vaughan et al., 1996, Nature Biotech., 14: 309) or synthetic libraries whereby germline V gene segments are 'rearranged' in vitro (Hoogenboom & Winter, 1992, J. Mol. Biol., 227: 381; Nissim et al., 1994, EMBO J., 13: 692; Griffiths et al., 1994, EMBO J., 13: 3245; De Kruif et al., 1995, J. Mol. Biol., 248: 97) or where synthetic CDRs are incorporated into a single rearranged V gene (Barbas et al., 1992. Proc. Natl. Acad. Sci. USA, 89: 4457). Most often, the antibody polypeptides displayed on the phage comprise antigen-binding antibody fragments, rather than whole conventional antibody molecules. As noted above, such fragments include, for example, heavy chain, light chain, heavy chain-light chain dimer, a Fab fragment, a F(ab')2 fragment, an Fv fragment, a scFv, or single immunoglobulin variable domains (see below). Methods for the preparation of phage display libraries displaying various antibody fragments are known to those of skill in the art. Such methods are also described, for example, in U.S. Pat. No. 6,696,245, which is incorporated herein by reference.

While the antigen binding unit of a naturally-occurring antibody (e.g., in humans and most other mammals) is generally known to be comprised of a pair of V regions ($V_L/V_H$), camelid species express a large proportion of fully functional, highly specific antibodies that are devoid of light chain sequences. The camelid heavy chain antibodies are found as homodimers of a single heavy chain, dimerized via their constant regions. The variable domains of these camelid heavy chain antibodies are referred to as $V_H$H domains and retain the ability, when isolated as fragments of the $V_H$ chain, to bind antigen with high specificity ((Hamers-Casterman et al., 1993, Nature 363: 446-448; Gahroudi et al., 1997, FEBS Lett. 414: 521-526). Antigen binding single $V_H$ domains have also been identified from, for example, a library of murine $V_H$ genes amplified from genomic DNA from the spleens of immunized mice and expressed in E. coli (Ward et al., 1989, Nature 341: 544-546). Ward et al. named the isolated single $V_H$ domains "dAbs," for "domain antibodies." The term "dAb" will refer herein to a single immunoglobulin variable domain ($V_H$ or $V_L$) polypeptide that specifically binds antigen. A "dAb" binds antigen independently of other V domains; however, a "dAb" can be present in a homo- or heteromultimer with other $V_H$ or $V_L$ domains where the other domains are not required for antigen binding by the dAb, i.e., where the dAb binds antigen independently of the additional $V_H$ or $V_L$ domains. The preparation of single immunoglobulin variable domains is described below.

A single immunoglobulin variable domain is a folded polypeptide domain which comprises sequences characteristic of immunoglobulin variable domains and which specifically binds an antigen (i.e., dissociation constant of 500 nM or less), and which binds antigen as a single variable domain; that is, without any complementary variable domain. An antibody single variable domain therefore includes complete antibody variable domains as well as modified variable domains, for example in which one or more loops have been replaced by sequences which are not characteristic of antibody variable domains or antibody variable domains which have been truncated or comprise N- or C-terminal extensions, as well as folded fragments of variable domains which retain a dissociation constant of 500 nM or less (e.g., 450 nM or less, 400 nM or less, 350 nM or less, 300 nM or less, 250 nM or less, 200 nM or less, 150 nM or less, 100 nM or less) and the target antigen specificity of the full-length domain. Preferably an antibody single variable domain useful in the invention is selected from the group of $V_H$ and $V_L$, including $V_{kappa}$ and $V_{lambda}$.

Single immunoglobulin variable domains are prepared in a number of ways. For each of these approaches, well-known methods of preparing (e.g., amplifying, mutating, etc.) and manipulating nucleic acid sequences are applicable.

One approach is to amplify and express the $V_H$ or $V_L$ region of a heavy chain or light chain gene for a cloned antibody known to bind the desired antigen. The boundaries of $V_H$ and $V_L$ domains, as well as other antibody polypeptide domains, are set out by Kabat et al., 1991, Sequences of Immunological Interest, 5$^{th}$ ed. U.S. Dept. Health & Human Services, Washington, D.C. The information regarding the boundaries of the $V_H$ and $V_L$ domains of heavy and light chain genes is used to design PCR primers that amplify the V domain from a cloned heavy or light chain coding sequence encoding an antibody known to bind a given antigen. The amplified V domain is inserted into a suitable expression vector, e.g., pHEN-1 (Hoogenboom et al., 1991, Nucleic Acids Res. 19: 4133-4137) and expressed, either alone or as a fusion with another polypeptide sequence. It is preferred, as described herein, that the V domain (or any other antibody domain) is expressed as a fusion with a GAS1 polypeptide signal sequence. The expressed $V_H$ or $V_L$ domain is then screened for high affinity binding to the desired antigen in isolation from the remainder of the heavy or light chain polypeptide. For all aspects of the present invention, screening for binding is performed as known in the art or as described herein below.

A phage displayed repertoire of $V_H$ or $V_L$ domains is screened by panning against the desired antigen. Methods for the construction of bacteriophage display libraries and lambda phage expression libraries are well known in the art, and taught, for example, by: McCafferty et al., 1990, Nature 348: 552; Kang et al., 1991, Proc. Natl. Acad. Sci. U.S.A., 88: 4363; Clackson et al., 1991, Nature 352: 624; Lowman et al., 1991, Biochemistry 30: 10832; Burton et al., 1991, Proc. Natl. Acad. Sci U.S.A. 88: 10134; Hoogenboom et al., 1991, Nucleic Acids Res. 19: 4133; Chang et al., 1991, J. Immunol. 147: 3610; Breitling et al., 1991, Gene 104: 147; Marks et al., 1991, J. Mol. Biol. 222: 581; Barbas et al., 1992, Proc. Natl. Acad. Sci. U.S.A. 89: 4457; Hawkins and Winter (1992) J. Immunol., 22: 867; Marks et al. (1992) J. Biol. Chem., 267: 16007; and Lerner et al. (1992) Science, 258: 1313. scFv phage libraries are taught, for example, by Huston et al., 1988, Proc. Natl. Acad. Sci U.S.A. 85: 5879-5883; Chaudhary et al., 1990, Proc. Natl. Acad. Sci U.S.A. 87: 1066-1070; McCafferty et al., 1990, supra; Clackson et al., 1991, supra; Marks et al., 1991, supra; Chiswell et al., 1992, Trends Biotech. 10: 80; and Marks et al., 1992, supra. Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra).

As noted, the repertoire of $V_H$ or $V_L$ domains can be a naturally-occurring repertoire of immunoglobulin sequences or a synthetic repertoire. A naturally-occurring repertoire is one prepared, for example, from immunoglobulin-expressing cells harvested from one or more animals, including humans. Such repertoires can be "naïve," i.e., prepared, for example, from human fetal or newborn immunoglobulin-expressing cells, or rearranged, i.e., prepared from, for example, adult human B cells. Natural repertoires are described, for example, by Marks et al., 1991, J. Mol. Biol. 222: 581 and Vaughan et al., 1996, Nature Biotech. 14: 309. If desired, clones identified from a natural repertoire, or any repertoire, for that matter, that bind the target antigen are then subjected to mutagenesis and further screening in order to produce and select variants with improved binding characteristics.

Synthetic repertoires of single immunoglobulin variable domains are prepared by artificially introducing diversity into a cloned V domain. Synthetic repertoires are described, for example, by Hoogenboom & Winter, 1992, J. Mol. Biol. 227: 381; Barbas et al., 1992, Proc. Natl. Acad. Sci. U.S.A. 89: 4457; Nissim et al., 1994, EMBO J. 13: 692; Griffiths et al., 1994, EMBO J. 13: 3245; DeKriuf et al., 1995, J. Mol. Biol. 248: 97; and WO 99/20749.

In one aspect, synthetic variable domain repertoires can be prepared in $V_H$ or Vκ backgrounds, based on artificially diversified germline $V_H$ or Vκ sequences. For example, the $V_H$ domain repertoire is based on cloned germline $V_H$ gene segments V3-23/DP47 (Tomlinson et al., 1992, J. Mol. Biol. 227: 7768) and JH4b. The $V_κ$ domain repertoire is based, for example, on germline $V_κ$ gene segments O2/O12/DPK9 (Cox et al., 1994, Eur. J. Immunol. 24: 827) and $J_κ 1$. Diversity is introduced into these or other gene segments by, for example, PCR mutagenesis. Diversity can be randomly introduced, for example, by error prone PCR (Hawkins, et al., 1992, J. Mol. Biol. 226: 889) or chemical mutagenesis. As discussed above, however it is preferred that the introduction of diversity is targeted to particular residues. It is further preferred that the desired residues are targeted by introduction of the codon NNK using mutagenic primers (using the IUPAC nomenclature, where N=G. A, T or C, and K=G or T), which encodes all amino acids and the TAG stop codon. Other codons which achieve similar ends are also of use, including the NNN codon (which leads to the production of the additional stop codons TGA and TAA), DVT codon ((A/G/T) (A/G/C)T), DVC codon ((A/G/T)(A/G/C)C), and DVY codon ((A/G/T)(A/G/C)(C/T). The DVT codon encodes 22% serine and 11% tyrosine, asparagine, glycine, alanine, aspartate, threonine and cysteine, which most closely mimics the distribution of amino acid residues for the antigen binding sites of natural human antibodies. Repertoires are made using PCR primers having the selected degenerate codon or codons at each site to be diversified. PCR mutagenesis is well known in the art; however, considerations for primer design and PCR mutagenesis useful in the methods of the invention are discussed herein in the section titled "PCR Mutagenesis."

Diversified repertoires are cloned into phage display vectors as fusions with a GAS1 secretion signal peptide as described herein. In general, the nucleic acid molecules and vector constructs required for the present invention are available in the art and are constructed and manipulated as set forth in standard laboratory manuals, such as Sambrook et al. (1989). *Molecular Cloning: A Laboratory Manual*, Cold Spring Harbor, USA.

Target Antigens

Target antigens for binding polypeptides as described herein are human antigens related to a disease or disorder. That is, target antigens as described herein are therapeutically relevant targets. A "therapeutically relevant target" is one which, when bound by a binding polypeptide, e.g., a single immunoglobulin variable domain or other antibody polypeptide that binds target antigen and acts as an antagonist or agonist of that target's activity, has a beneficial effect on the human individual in which the target is bound. A "beneficial effect" is demonstrated by at least a 10% improvement in one or more clinical indicia of a disease or disorder, or, alternatively, where a prophylactic use of the binding polypeptide is desired, by an increase of at least 10% in the time before symptoms of the targeted disease or disorder are observed, relative to an individual not treated with the binding polypeptide preparation. Non-limiting examples of antigens that are suitable targets for binding polypeptides as described herein include cytokines, cytokine receptors, enzymes, enzyme cofactors, or DNA binding proteins. Suitable cytokines and growth factors include but are not limited to: ApoE, Apo-SAA, BDNF, Cardiotrophin-1, EGF, EGF receptor, ENA-78, Eotaxin, Eotaxin-2, Exodus-2, FGF-acidic, FGF-basic, fibroblast growth factor-10, FLT3 ligand, Fractalkine (CX3C), GDNF, G-CSF, GM-CSF, GF-β1, insulin, IFN-g, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TACE recognition site, TGF-α, TGF-β, TGF-β2, TGF-β3, tumor necrosis factor (TNF), TNF-α, TNF-β, TNF receptor I (p55), TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3 and HER 4. Cytokine receptors include receptors for each of the foregoing cytokines, e.g., IL-1R, IL-6R, IL-10R, IL-18R, etc. It will be appreciated that this list is by no means exhaustive.

Producing a Selected Polypeptide:

Once a polypeptide is selected from a library of GAS1 secretion signal peptide fusion polypeptides expressed as phage display packages, that phage can be used to generate more of the polypeptide. In one aspect, the phage itself can be used to infect fresh cells, thereby producing the polypeptide. In another aspect, the coding sequence can be excised, along with the GAS1 secretion signal peptide, from the phage nucleic acid (e.g., by restriction digestion or by PCR amplification) and inserted into an appropriate expression vector. In this instance, where the expression vector is introduced to a prokaryotic host cell, e.g., E. coli, the GAS1 secretion signal peptide will direct the secretion of the polypeptide into the periplasmic space. In the alternative, where the host cell is, for example, a yeast cell, such as S. cerevisiae, the GAS1 secretion signal polypeptide will direct the secretion of the polypeptide to the medium. Suitable vectors and host cell systems for high level protein production are widely known and can be selected by one of skill in the art.

In general terms, one can produce a desired polypeptide by introducing a vector encoding that polypeptide under the control of a strong or inducible promoter into an appropriate host cell, and culturing the host cell under conditions such that the polypeptide is produced. In one aspect, where the desired polypeptide is an antibody polypeptide that comprises both a VH and a VL polypeptide, the method involves culturing a host cell transformed with a vector encoding a dicistronic construct, having one prokaryotic promoter driving expression of sequences encoding a VH and a VL, each of which is fused to a GAS1 secretion signal peptide, under conditions such that the VH and VL polypeptides sequences are expressed. A similar approach is warranted where the construct encodes only a VH or a VL sequence fused to GAS1 secretion signal peptide, i.e., a monocistronic construct. Methods of protein purification are well known to those of skill in the art.

EXAMPLES

Example 1

Selection of Eukaryotic Signal Peptides

Yeast GAS1 signal peptide was identified as a candidate secretion signal peptide suitable for use in fusion protein expression in both eukaryotic and prokaryotic cells. In one aspect, it was desired to maximize fusion protein expression in E. coli cells. E. coli use a specific subset of the 61 available amino acid codons for the production of most mRNA molecules (Wada et al. 1992 NAR 20 p 2111). The initial signal peptide coding regions were optimized according to this E. coli codon usage (see FIG. 1) using Vector NTI v7 (InVitrogen). Codon usage was modified to optimize the A/T-rich nature of the signal peptide coding sequence—each nucleotide that could be changed to an A or T without modifying the amino acid encoded was changed.

Example 2

Comparison of Eukaryotic Signal Peptides

Eukaryotic leader signal peptides from yeast glucan 1,3-β-glucosidase precursor and the salmon gonadotropin b-I chain precursor were cloned into a pUC119 based expression vector under control of the lacZ promoter (FIG. 2) for comparison to the yeast GAS1 signal peptide. The signal peptides were compared for their ability to secrete dAb HEL4 into the periplasm. The supernatants of these clones were tested in a lysozyme binding ELISA (FIG. 3). The values in FIG. 3 are the means of four independent cultures tested. The GAS signal peptide with the AT rich nucleotide sequence produced the best ELISA signals and this variant of GAS leader was used in all subsequent experiments described below.

Example 3

Expression Level of Eukaryotic Signal Peptides

The expression levels of dAb HEL4 were determined when produced with the GAS (AT rich) versus the Gene 3 signal peptide. The expression of the dAbs was induced in 50 ml cultures and dAbs were purified from the supernatant using protein A Sepharose in a batch-wise manner. The purified dAbs were analyzed on SDS-PAGE (FIG. 4). The GAS signal peptide gave a yield of 32 mg/l which was 2-fold better than the 14 mg/l yield obtained using the Gene3 signal peptide. The GAS signal peptide has now been used to express more than 100 different dAbs. The expression levels vary between 1 and 50 mg/l culture supernatant. Differences in expression level are mainly due to the sequence of the particular dAb expressed.

Example 4

Accurate Processing and Cleavage of GAS Signal Peptide

Purified dAbs produced with the GAS (AT rich) signal peptide were used for N-terminal sequence and mass spectrometry analysis. Sequencing of protein bands blotted from reducing SDS-PAGE gave the expected N terminal sequence "STDIQ$^c$ (SEQ ID NO: 5). This is the expected sequence, as the dAbs used are preceded by Ser-Thr residues which are present in the poly linker to accommodate a SalI cloning site.

Mass spectrometry showed predominantly the presence of a full length, correctly processed dAb including the C-terminal 8×HIS and VSV tags with a Molecular Weight of 15669 Daltons. This differs by less than 0.01% of the predicted value (MW=15671). The N-terminal sequencing and the Mass spectrometry show that dAbs produced with a GAS signal peptide are correctly processed and cleaved (data not shown).

Example 5

Similar Specific Activity with GAS Signal Peptide

The specific activity of dAb HEL4 produced with the GAS (AT rich) or the gene3 signal peptide was compared in an antigen binding ELISA (FIG. 5). This shows that dAb HEL4 produced with GAS has a better specific activity compared to that produced with the gene3 signal peptide. The decrease in specific activity is due to the presence of the N-terminal FLAG tag which affects the binding of HEL4 to lysozyme. This decrease has been observed with HEL4 in our laboratory and is independent of the signal peptide that is used.

Example 6

GAS Signal Peptide Functions in Fd Phage

The GAS (AT rich) signal peptide was cloned into an Fd phage vector to replace the naturally occurring gene3 signal peptide. This GAS signal peptide was tested for its ability to produce phage particles and was compared with the gene3 signal peptide. The supernatants produced from the clones were tested in ELISA assays for binding to lysozyme or to the anti-myc antibody. FIG. 6 shows that phages produced with either the GAS or gene3 signal peptide have an almost identical binding pattern in ELISA. This shows that the display levels of dAbs on the phage are very similar for the GAS and gene3 signal peptide.

Example 7

Phage Library with GAS Signal Peptide in Fd Phage

A large phage library was constructed using the phage vector with a GAS (AT rich) signal peptide and a C-terminal myc tag. Diversity was introduced by randomly combining CDR1, CDR2 and CDR3 using assembly PCR. The library was pre-selected using protein A or protein L (which bind correctly folded dAbs) followed again by random combinatorial assembly of the CDR regions. This approach resulted in the largest one-vector phage library to date, with a size of $3.3 \times 10^{10}$ of which the majority (52%) is functional.

Figure 7B:
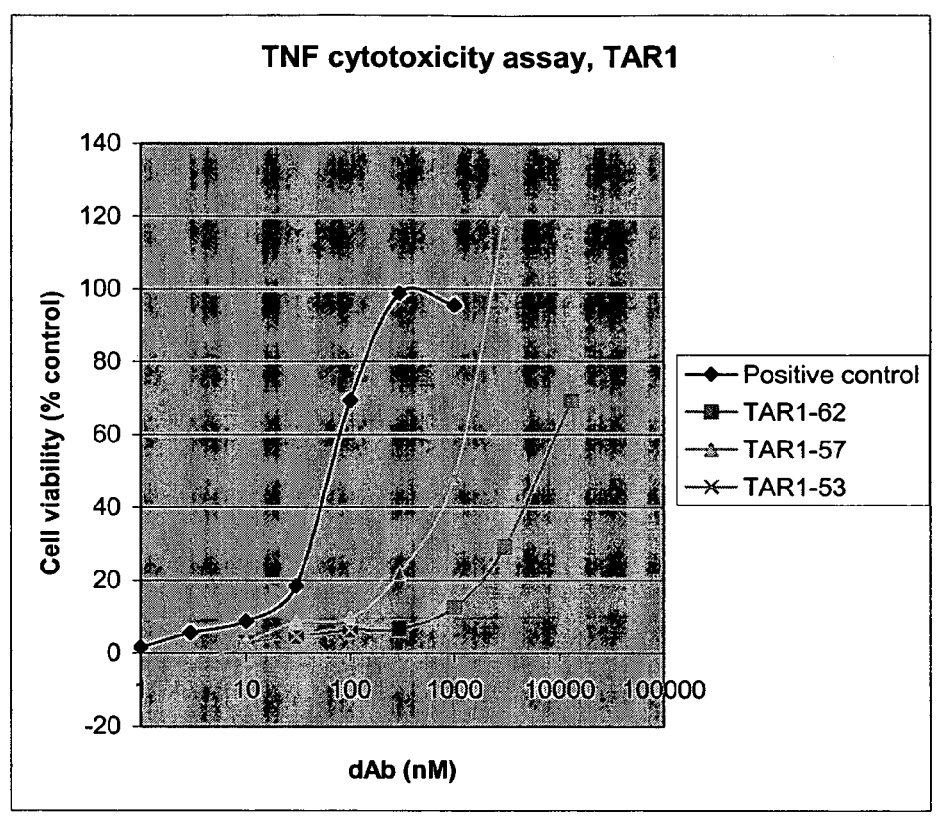

This library was used to select against seven different protein antigens and yielded at least 10 different binders against each antigen. The affinities of the selected dAbs vary between 20 μm and 10 nM. Several dAb clones with functional activity (e. g. blockade of binding of the target to its ligand) were isolated against most of the targets. One example of these targets is human TNF-α. The isolated dAbs bind TNF-α specifically and block the binding of TNF-α to its receptor TNF R1. This has been shown in ELISA-based assays (see below) as well as a cell-based assay using the L929 cell-line (described below; see FIG. 7). Similar results have been obtained with a number of other cytokine targets.

In another series of experiments, a similar library construction approach was used to generate an even larger library. The library was constructed using the fd phage vector with a GAS (AT rich) signal peptide and a C-terminal myc tag. Diversity was again introduced by randomly combining CDR1, CDR2 and CDR3 using assembly PCR. The library was pre-selected using protein A or protein L, and an additional pre-selection for thermodynamically stable clones was added, involving 80° C. heat treatment of the phage followed by selection on protein A or protein L. This library was screened against eight antigens, resulting in the identification of different dAbs specific for each antigen, each dAb having an $IC_{50}$ or $K_D$ in the low micromolar to low nanomolar range. The antigens included: TNFR1 (2 different dAbs identified); TNF (6 different dAbs identified); MSA (mouse serum albumin; 4 different dAbs identified); RSA (rat serum albumin; 5 different dabs identified); HSA (human serum albumin; 7 different dAbs identified); CD40L (9 different dAbs identified); IL-4 (20 different dAbs identified); and IL-13 (5 different dAbs identified).

Elisa for inhibition of TNA-α binding:

Anti-TNF-α dAbs were tested for the ability to inhibit the binding of TNF-α to recombinant TNF receptor 1 (p55). Briefly, Maxisorp plates were incubated overnight with 30 mg/ml anti-human Fc mouse monoclonal antibody (Zymed, San Francisco, USA). The wells were washed with phosphate buffered saline (PBS) containing 0.05% Tween-20 and then blocked with 1% BSA in PBS before being incubated with 100 ng/ml TNF receptor 1 Fc fusion protein (R&D Systems, Minneapolis, USA). Anti-TNF-α dAb was mixed with TNF-α which was then added to the washed wells at a final concentration of 10 ng/ml. TNF-α binding was detected with 0.2 mg/ml biotinylated anti-TNF-α antibody (HyCult biotechnology, Uben, Netherlands) followed by 1 in 500 dilution of horse radish peroxidase labelled streptavidin (Amersham Biosciences, UK) and incubation with TMB substrate (KPL, Gaithersburg, Md.). The reaction was stopped by the addition of HCl and the absorbance was read at 450 nm. Anti-TNF-α dAb inhibitory activity leads to a decrease in TNF-α binding, and therefore to a decrease in absorbance compared with the TNF-α only control.

L929 Cytotoxicity Assay:

Anti-TNF-α dAbs were tested for the ability to neutralize the cytotoxic activity of TNF-α on mouse L929 fibroblasts (Evans, T. (2000) Molecular Biotechnology 15, 243-248). Briefly, L929 cells plated in microtiter plates were incubated overnight with anti-TNF-α dAbs, 100 pg/ml TNF-α and 1 mg/ml actinomycin D (Sigma, Poole, UK). Cell viability was measured by reading absorbance at 490 nm following an incubation with [3-(4,5-dimethylthiazol-2-yl)-5-(3-carboxymethoxyphenyl)-2-(4-sulfophenyl)-2H-tetrazolium (Promega, Madison, USA). Anti-TNF-α dAb activity leads to a decrease in TNF-α cytotoxicity and therefore an increase in absorbance compared with the TNF-α only control.

The invention claimed is:

1. A bacteriophage comprising a polynucleotide molecule comprising a promoter operably linked to a nucleic acid sequence encoding, in operable linkage: a GAS1 secretion signal sequence selected from the group consisting of the nucleic acid shown in SEQ ID NO: 3 and SEQ ID NO: 4, an immunoglobulin variable domain polypeptide, and a bacteriophage coat protein.

2. The bacteriophage according to claim 1, wherein said immunoglobulin variable domain comprises a light chain variable domain.

3. The bacteriophage according to claim 1, wherein said immunoglobulin variable domain comprises a heavy chain variable domain.

4. The bacteriophage according to claim 1, wherein the sequence encoding the GAS 1 secretion signal sequence is operably linked at its 3' end to a sequence encoding a bacteriophage coat protein.

5. The bacteriophage according to claim 1, wherein the sequence encoding the GAS1 secretion signal sequence is operably linked at its 3' end to a sequence encoding an immunoglobulin variable domain polypeptide.

6. The bacteriophage according to claim 1, wherein the polynucleotide molecule comprising a dicistronic transcription unit comprising a nucleic acid encoding an immunoglobulin heavy chain variable domain and an immunoglobulin light chain variable domain, the 5' end of each of said immunoglobulin heavy and light chain variable domains being linked to the 3' end of a respective nucleic acid sequence encoding a GAS 1 secretion signal polypeptide.

7. The bacteriophage according to claim 6, wherein the dicistronic transcription unit is operably linked to a prokaryotic promoter sequence.

8. The bacteriophage according to claim 1, wherein a restriction enzyme recognition site is interposed between the nucleic acid sequence encoding the GAS 1 secretion signal peptide and the sequence encoding the immunoglobulin variable domain.

9. The bacteriophage according to claim 1, comprising a promoter operably linked to the sequence encoding the GAS 1 secretion signal peptide, wherein said promoter is other than a rhamnose promoter.

10. The bacteriophage according to claim 1, further comprising a polypeptide encoded by a polynucleotide molecule comprising a promoter operably linked to a nucleic acid sequence encoding, in operable linkage: a GAS1 secretion signal sequence, an immunoglobulin variable domain polypeptide, and a bacteriophage coat protein.

* * * * *

SEQUENCE LISTING

<160> NUMBER OF SEQ ID NOS: 15

<210> SEQ ID NO 1
<211> LENGTH: 66
<212> TYPE: DNA
<213> ORGANISM: Saccharomyces cerevisiae

<400> SEQUENCE: 1
atgttgttta atccctttc aaagttagca accgctgctg cttttttgc tggcgtcgca      60 actgcg                                                               66

<210> SEQ ID NO 2
<211> LENGTH: 22
<212> TYPE: PRT
<213> ORGANISM: Saccharomyces cerevisiae

<400> SEQUENCE: 2

Met Leu Phe Lys Ser Leu Ser Lys Leu Ala Thr Ala Ala Ala Phe Phe
 1               5                  10                  15

Ala Gly Val Ala Thr Ala
            20

<210> SEQ ID NO 3
<211> LENGTH: 66
<212> TYPE: DNA
<213> ORGANISM: Artificial Sequence
<220> FEATURE:
<223> OTHER INFORMATION: S. cerevisiae GAS leader sequence optimized for
      expression in E. coli

<400> SEQUENCE: 3
atgctgttta aaagcctgag caaactggcg accgcggcgg cgttttttgc gggcgtggcg      60
accgcg                                                                66

<210> SEQ ID NO 4
<211> LENGTH: 66
<212> TYPE: DNA
<213> ORGANISM: Artificial Sequence
<220> FEATURE:
<223> OTHER INFORMATION: S. cerevisiae GAS leader nucleotide sequence
      modified for optimal expression

<400> SEQUENCE: 4
atgttattta aatcattatc aaaattagca accgcagcag catttttgc aggcgtggca      60 acagcg                                                                66

<210> SEQ ID NO 5
<211> LENGTH: 18
<212> TYPE: PRT
<213> ORGANISM: Bacteriophage M13mp18

<400> SEQUENCE: 5

Met Lys Lys Leu Leu Phe Ala Ile Pro Leu Val Val Pro Phe Tyr Ser
 1               5                  10                  15

His Ser

<210> SEQ ID NO 6
<211> LENGTH: 20
<212> TYPE: PRT
<213> ORGANISM: Escherichia coli

```
<400> SEQUENCE: 6

Met Arg Ala Lys Leu Leu Gly Ile Val Leu Thr Thr Pro Ile Ala Ile
1               5                   10                  15

Ser Ser Phe Ala
            20

<210> SEQ ID NO 7
<211> LENGTH: 21
<212> TYPE: PRT
<213> ORGANISM: Amorphotheca resinae

<400> SEQUENCE: 7

Met Arg Leu Leu Pro Ser Ser Cys Ala Gly Ala Leu Ser Leu Leu Cys
1               5                   10                  15

Ser Leu Ala Ile Ala
            20

<210> SEQ ID NO 8
<211> LENGTH: 21
<212> TYPE: PRT
<213> ORGANISM: Chlamydomonas sp.

<400> SEQUENCE: 8

Met Gly Ala Leu Ala Val Phe Ala Val Ala Cys Leu Ala Ala Val Ala
1               5                   10                  15

Ser Val Ala His Ala
            20

<210> SEQ ID NO 9
<211> LENGTH: 21
<212> TYPE: PRT
<213> ORGANISM: Drosophila melanogaster

<400> SEQUENCE: 9

Met Ala Leu Val Arg Val Ser Cys Met Leu Ala Leu Leu Leu Ile Ala
1               5                   10                  15

Gly Gln Gly Gln Ala
            20

<210> SEQ ID NO 10
<211> LENGTH: 22
<212> TYPE: PRT
<213> ORGANISM: Rhizopus microsporus

<400> SEQUENCE: 10

Met Leu Ala Arg Thr Phe Leu Gly Met Ala Ile Ser Ala Phe Leu Ala
1               5                   10                  15

Ser Thr Gly Val Gln Ala
            20

<210> SEQ ID NO 11
<211> LENGTH: 23
<212> TYPE: PRT
<213> ORGANISM: Saccharomyces cerevisiae

<400> SEQUENCE: 11

Met Arg Phe Ser Thr Thr Leu Ala Thr Ala Ala Thr Ala Leu Phe Phe
1               5                   10                  15

Thr Ala Ser Gln Val Ser Ala
            20
```

```
<210> SEQ ID NO 12
<211> LENGTH: 23
<212> TYPE: PRT
<213> ORGANISM: Triticum aestivum

<400> SEQUENCE: 12

Met Gly Tyr Ser Lys Thr Leu Val Ala Gly Leu Phe Ala Met Leu Leu
1               5                   10                  15

Leu Ala Pro Ala Val Leu Ala
            20

<210> SEQ ID NO 13
<211> LENGTH: 24
<212> TYPE: PRT
<213> ORGANISM: Rattus rattus

<400> SEQUENCE: 13

Met Thr Ser Arg Met Ala Ile Leu Ser Gly Leu Leu Phe Trp Leu Leu
1               5                   10                  15

Leu Glu Trp Asn Pro Ala Phe Ala
            20

<210> SEQ ID NO 14
<211> LENGTH: 24
<212> TYPE: PRT
<213> ORGANISM: Nicotiana tabacum

<400> SEQUENCE: 14

Met Asn Ile Lys Val Ser Leu Leu Phe Ile Leu Pro Ile Phe Leu Leu
1               5                   10                  15

Leu Leu Thr Ser Lys Val Lys Ala
            20

<210> SEQ ID NO 15
<211> LENGTH: 24
<212> TYPE: PRT
<213> ORGANISM: Oncorhynchus keta

<400> SEQUENCE: 15

Met Tyr Cys Thr His Leu Met Thr Leu Gln Leu Val Val Met Ala Met
1               5                   10                  15

Leu Trp Val Thr Pro Val Arg Ala
            20
```